United States Patent
Apple et al.

[11] Patent Number: 6,162,165
[45] Date of Patent: Dec. 19, 2000

[54] MEDICAL RADIATION TREATMENT DEVICE

[75] Inventors: Marc G. Apple, Fort Wayne; Brian L. Bates; John A. DeFord, both of Bloomington; Neal E. Fearnot, West Lafayette, all of Ind.

[73] Assignees: Cook Incorporated, Bloomington; MED Institute, Inc., West Lafayette, both of Ind.

[21] Appl. No.: 09/203,947

[22] Filed: Dec. 2, 1998

Related U.S. Application Data

[60] Provisional application No. 60/067,604, Dec. 5, 1997.

[51] Int. Cl.$^7$ .................................................. A61N 5/00
[52] U.S. Cl. ...................................................... 600/3
[58] Field of Search .............................................. 600/1–8

[56] References Cited

U.S. PATENT DOCUMENTS

| | | |
|---|---|---|
| 3,324,847 | 6/1967 | Zoumboulis . |
| 3,438,365 | 4/1969 | Packer et al. . |
| 3,673,411 | 6/1972 | Glasser . |
| 3,848,773 | 11/1974 | Adler et al. . |
| 4,192,438 | 3/1980 | Foster et al. . |
| 4,241,728 | 12/1980 | Mirell . |
| 4,330,507 | 5/1982 | Lewis . |
| 4,364,376 | 12/1982 | Bigham . |
| 4,497,349 | 2/1985 | Farley . |
| 4,565,301 | 1/1986 | Hubbard et al. . |
| 4,615,468 | 10/1986 | Gay . |
| 4,801,047 | 1/1989 | Klatte et al. . |
| 5,059,166 | 10/1991 | Fischell et al. . |
| 5,199,939 | 4/1993 | Dake et al. . |
| 5,213,561 | 5/1993 | Weinstein et al. . |
| 5,302,168 | 4/1994 | Hess . |
| 5,427,104 | 6/1995 | Briend et al. . |
| 5,429,582 | 7/1995 | Williams . |
| 5,485,835 | 1/1996 | Vande Streek et al. . |
| 5,611,767 | 3/1997 | Williams . |
| 5,616,114 | 4/1997 | Thornton et al. . |
| 5,707,332 | 1/1998 | Weinberger . |
| 5,782,740 | 7/1998 | Schneiderman . |
| 5,782,742 | 7/1998 | Crocker et al. . |
| 5,840,008 | 11/1998 | Klein et al. . |
| 5,916,143 | 6/1999 | Apple et al. .................... 600/3 |
| 5,947,890 | 9/1999 | Spencer et al. .................. 600/3 |
| 5,971,909 | 10/1999 | Bradshaw et al. ............... 600/3 |

FOREIGN PATENT DOCUMENTS

| | | |
|---|---|---|
| 999263 | 11/1976 | Canada . |
| 0688580 | 12/1995 | European Pat. Off. . |
| 9001208 | 2/1990 | WIPO . |
| 9304735 | 3/1993 | WIPO . |
| 9740889 | 11/1997 | WIPO . |
| 9825674 | 6/1998 | WIPO . |
| 9912609 | 3/1999 | WIPO . |

OTHER PUBLICATIONS

Gutkowski, et al., *Journal of Nuclear Medicine*, A Calibrated Dose Dispenser For Gaseous $^{133}$Xe, vol. 16, No. 12, Dec. 1975, pp. 1197–1199.

*Primary Examiner*—Cary O'Connor
*Assistant Examiner*—Catherine E McPherson
*Attorney, Agent, or Firm*—Richard J. Godlewski; Anton P. Ness

[57] ABSTRACT

A catheter apparatus and radiation dosimetry unit indicator for delivery of a prescribed radiation dose to a patient. The catheter is filled with a radiation carrier material such as an inert radioactive gas for the treatment of, for example, restenosis after angioplasty, and malignancies. The inflated catheter includes a plurality of discrete chambers for transporting the radioactive carrier material, and a plurality of discrete chambers enabling substantial blood flow through the artery during treatment with the prescribed radiation. The inflated catheter can also comprise a one-unit balloon. A specific metal coating enhances the radiation dose delivered to the target. The wall of the inflation lumen attenuates transmission dose to the blood circulating through the hollow inner lumen of the catheter device. The system also creates increased by-product radiation, from the impact of beta particles and gamma protons traveling toward the lumen wall. A radiation dosimetry unit indicator is positioned, disposed, or affixed to a calibrated catheter to assist the physician in prescribing radiation activity and exposure times.

19 Claims, 13 Drawing Sheets

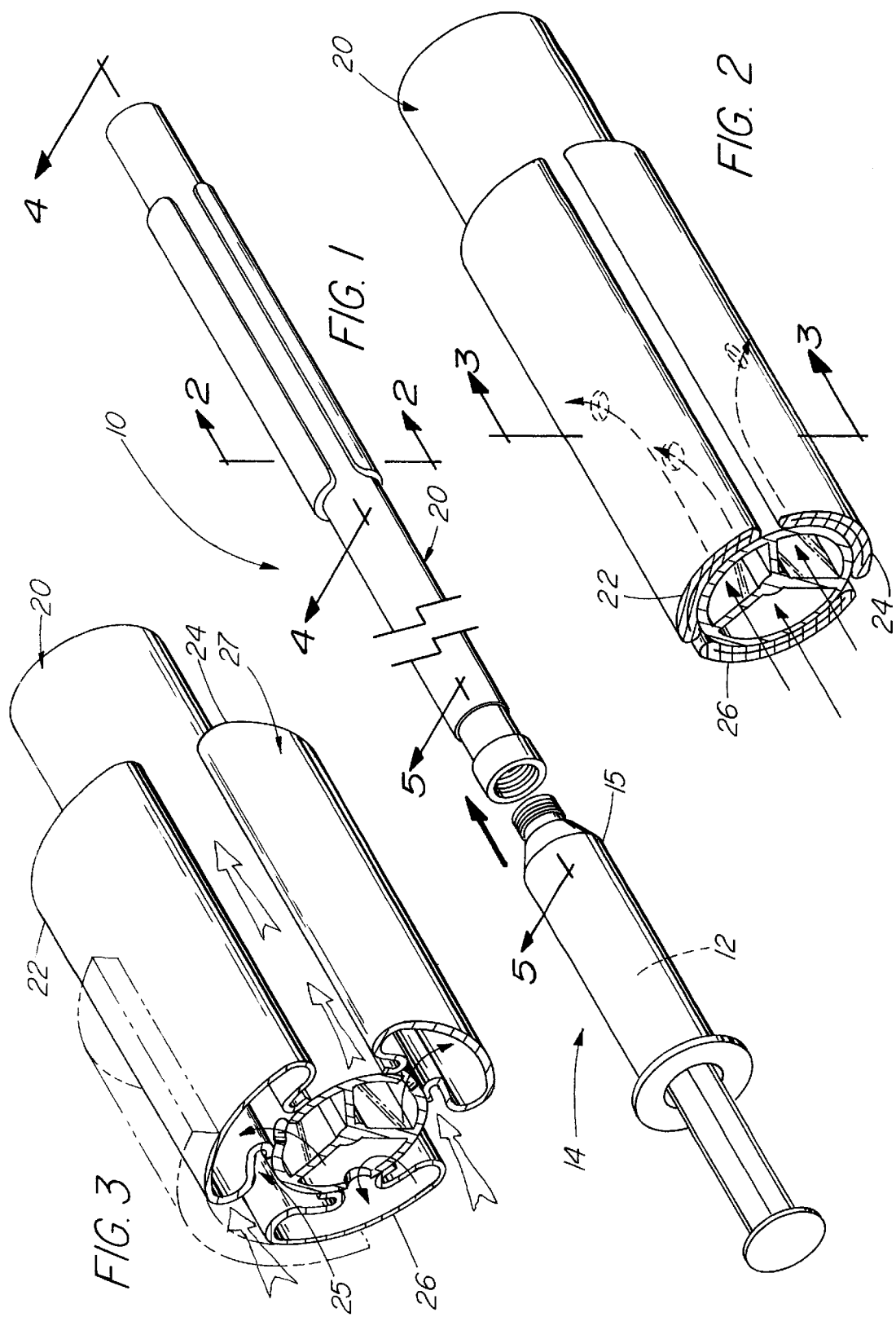

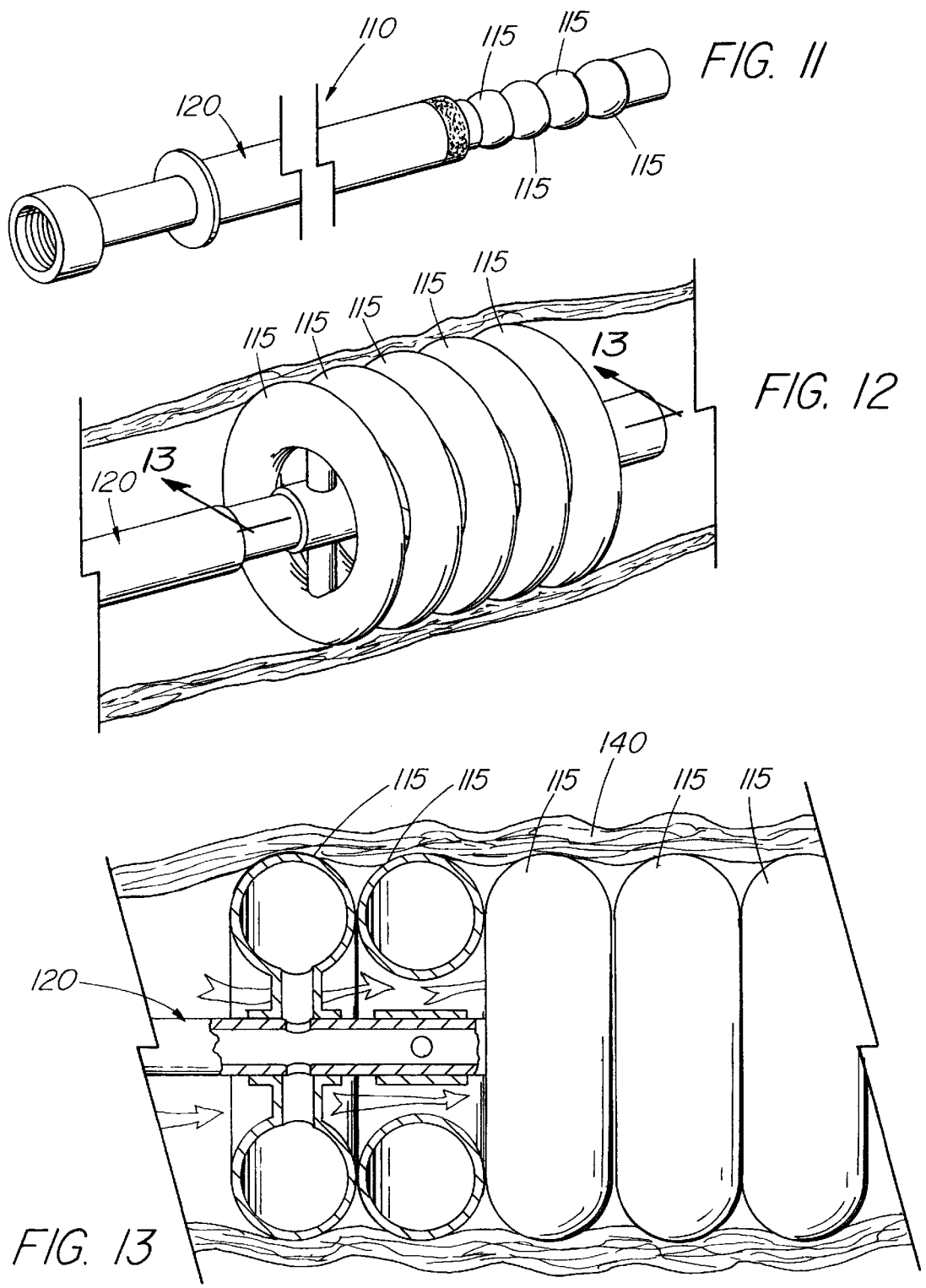

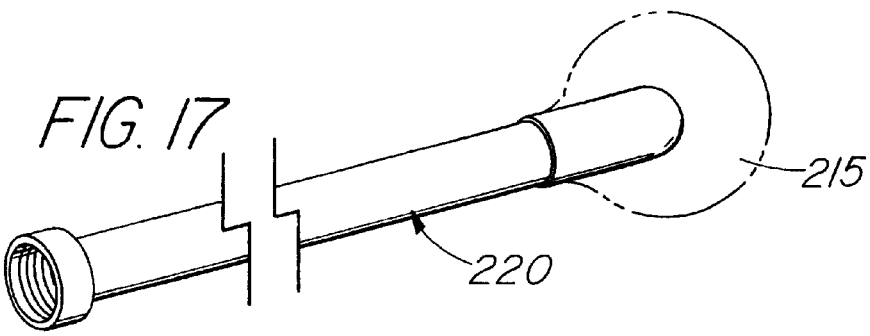
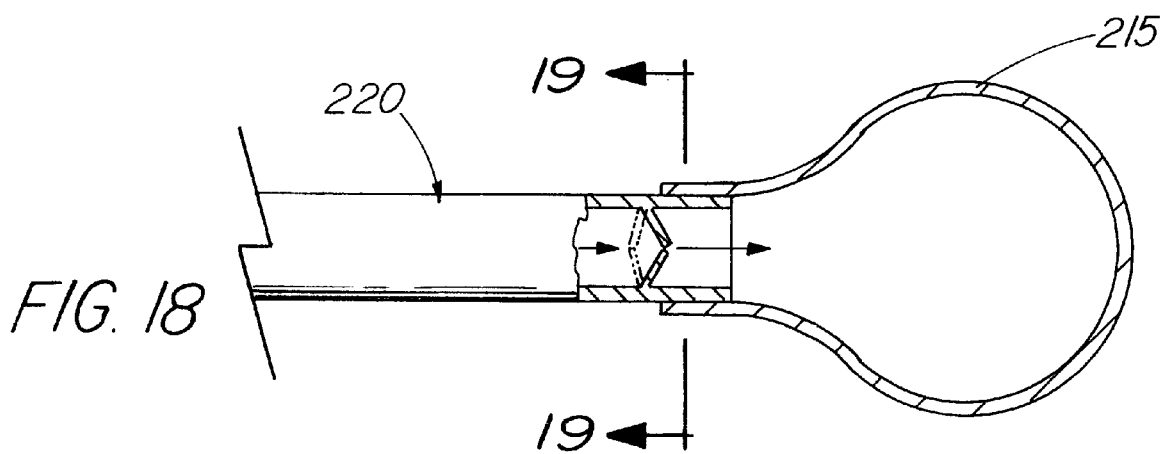
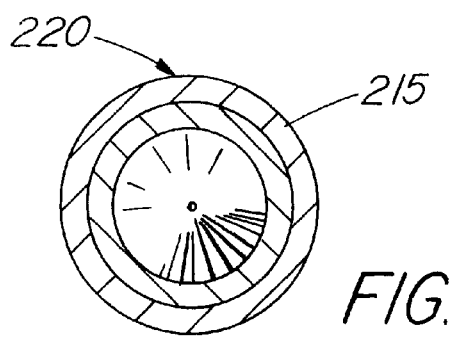

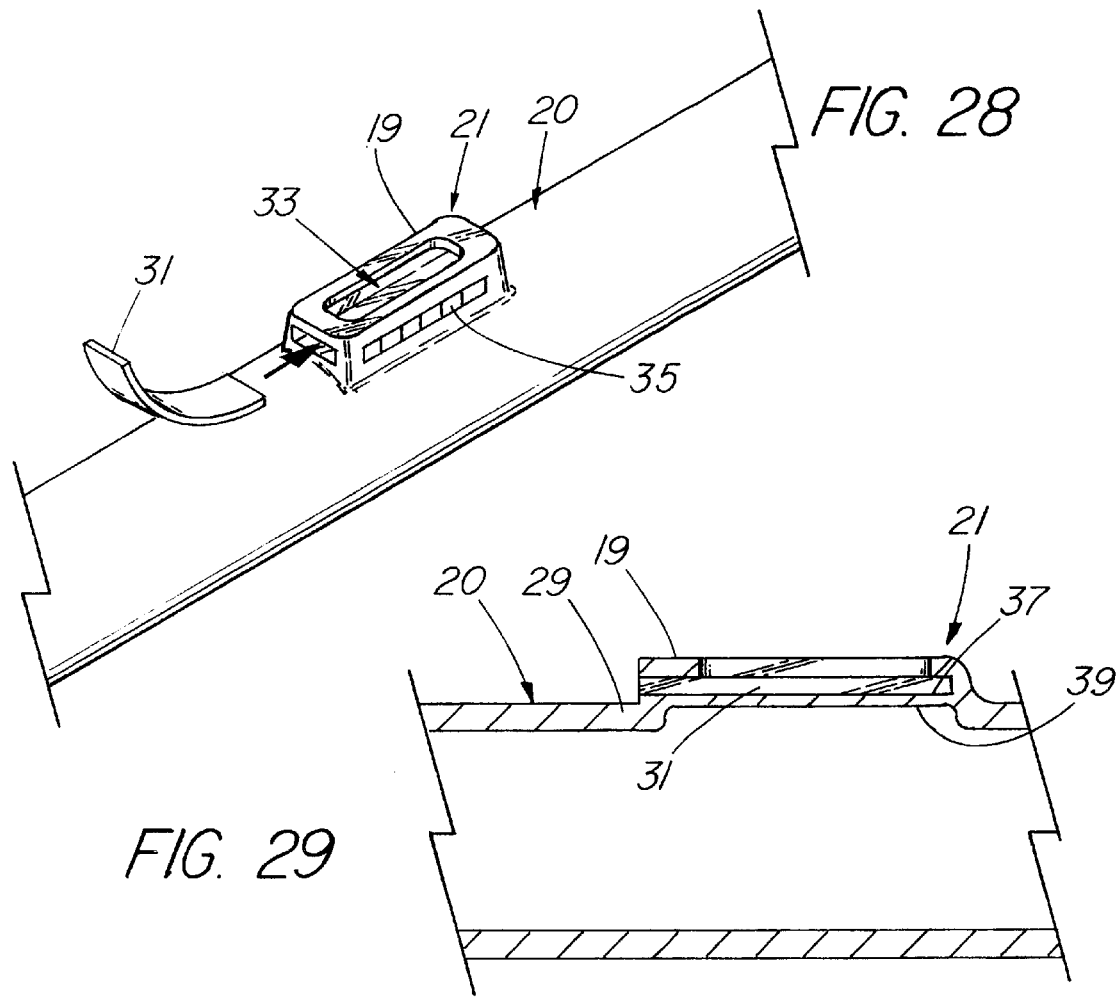
FIG. 28
FIG. 29
FIG. 30
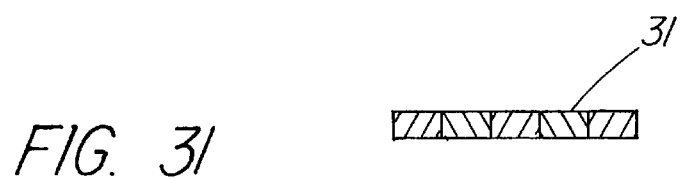
FIG. 31

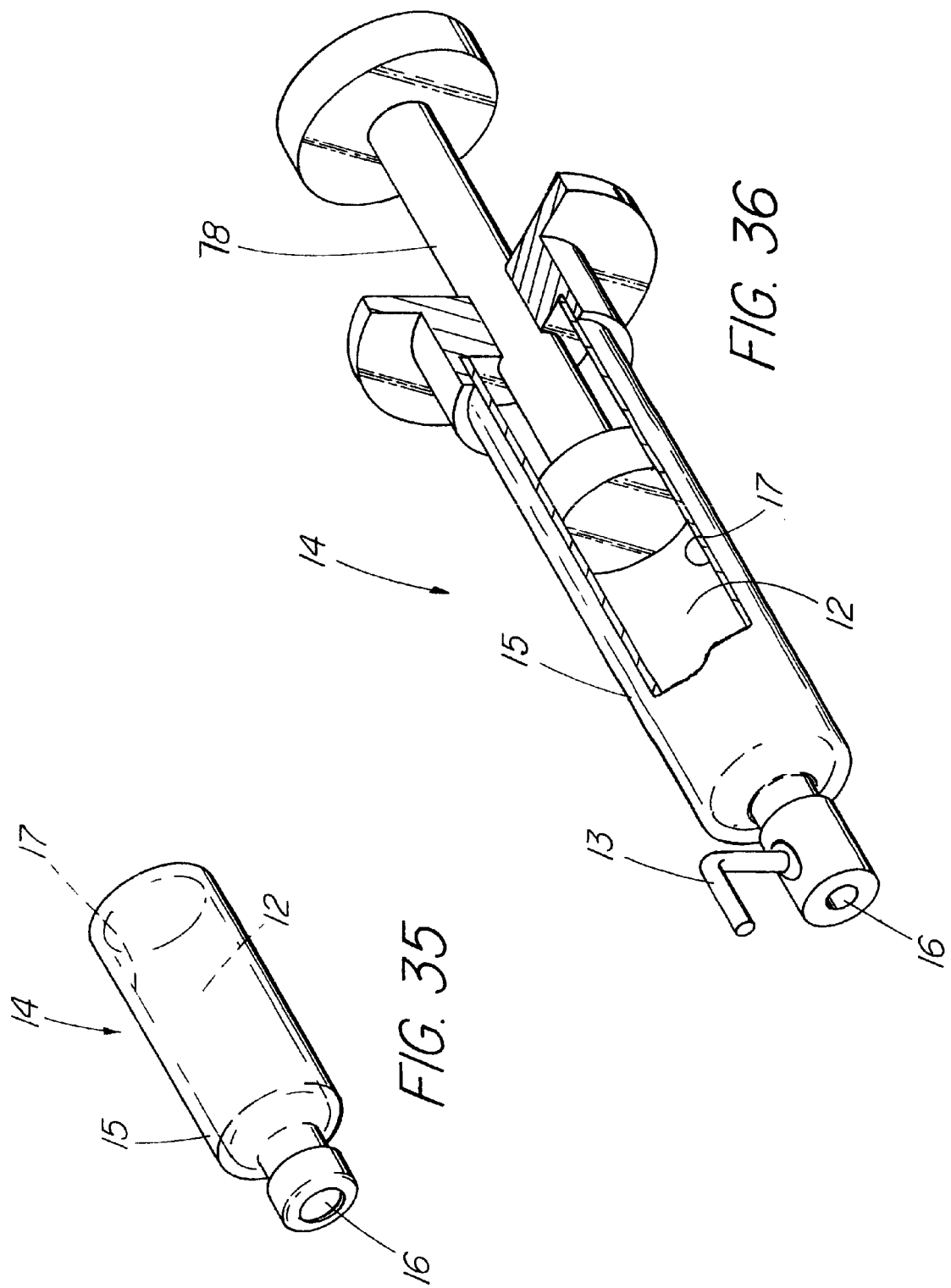

MEDICAL RADIATION TREATMENT DEVICE

CROSS REFERENCE TO RELATED APPLICATIONS

This application claims priority of provisional application Ser. No. 60/067,604, filed Dec. 5, 1997.

TECHNICAL FIELD

This invention relates generally to medical devices and, in particular, to medical radiation treatment devices such as a sealed container and the like for delivering a radiation treatment to a patient.

BACKGROUND OF THE INVENTION

Angioplasty is an established procedure for reducing the effect of atherosclerotic plaque on and intraluminal narrowing of the arterial walls within the vascular system of the patient. The effect is reduced by use of a catheter that is inserted into the site of the diseased-occluded vessel. A balloon portion of the catheter is then inflated to a predetermined pressure range and size, to radially compress the plaque occlusion, thereby increasing the internal diameter of the previously restricted artery. The balloon is then collapsed and the catheter is removed.

After the angioplasty procedure has been performed, as many as one-third to one-half of the patients soon develop restenosis. Restenosis can occur after angioplasty or other recannulation procedures, with or without stenting, wherein the migration and proliferation of benign cells cause a restenotic lesion to form, resulting in the further blockage of the intravascular structure.

Radiation is administered to patients for a variety of reasons, such as to treat restenosis, malignant or benign tumors, or the like. Examples of such treatments are disclosed in U.S. Pat. Nos. 5,059,166; 5,213,561; and 5,302,168.

It would be preferred to be able to provide a radiation delivery system which would:

a) deliver a predetermined totally-cumulative and homogeneous dose of radiation to the lesion site, at a predetermined penetration depth, while minimizing the exposure of surrounding healthy tissue to the radiation;

b) enable the treating physician or other health-care personnel to be bedside to the patient during the administration of the radiation therapy without exposing the physician or health care personnel to any unreasonable risk;

c) use radiation material that is readily and inexpensively available from a commercial provider;

d) use minimal special equipment storage, or delivery devices, except for routine facilities available in most nuclear medicine or radiation oncology departments;

e) use a radiation carrier material that if applied as an unsealed free-gas form, the inert, noble gas properties essentially enable the molecules of the carrier material to rapidly dissipate throughout the body of the patient without any prolonged organ accumulation or chemical interaction, and rapid dilution of the carrier material is quickly re-released from the bloodstream through the lungs;

f) minimize long term occlusion of normal blood flow during therapy, thereby providing more flexibility as to administration time and dosage;

g) use a radiation carrier material that is stable and which can be pressurized, stored, and made to high millicurie activity per cubic centimeter with reasonable cost and availability;

h) use beta particles having excellent initial dose rate delivery and energy transfer when directly adjacent to the targeted tissue within the first one millimeter, and not penetrate much beyond this depth;

i) use gamma photon energies having depth doses that provide complementary dose deposition with the beta particles for the first one millimeter, and primary additive dose delivery for an additional two to three millimeters of the targeted tissue;

j) use these beneficial physical and biological radiation properties for treating restenosis, and malignancies (for example—in the brain, lung, esophagus, trachea, cervix, biliary ductal system, colon or rectum, the gastrointestinal system, the gynecological system, or head and neck) and other internal ailments where an internal application of radiation directly applied to the tissue may be needed; and k) attenuate the transmission dose to blood circulating through the apparatus, and while creating increased by-product radiation, delivering useful radiation dose over hundreds of micrometers of target tissue.

SUMMARY OF THE INVENTION

The foregoing problems are solved and a technical advance is achieved in an illustrative medical radiation treatment device such as a sealed container, preferably fluid or gas-tight, having an interior volume in the range of 0 to 10 cubic centimeters and a radioactive fluid contained therein and having a specific concentration in a range of 50 to 500 millicuries per cubic centimeter (preferably 100 to 150 millicuries per cubic centimeter) for administering a radiation treatment to a treatment site such as the coronary vessels of a patient. As a result, total activity in the range of 200 to 450 millicuries (preferably 300 to 400 millicuries) per administration can be advantageously delivered to the treatment site. For coronary applications, a dose rate of 250 to 750 centiGray (cGy) per minute (preferably 400 to 500 cGy per minute) for approximately 2 minutes can advantageously be delivered homogeneously to a tissue treatment site at a preferred depth of 0.25 mm via, for example, a compatible inflated balloon catheter. As a result, a total dose of 500 to 1500 cGy can be advantageously delivered for the most effective total dose as a result of human trials and porcine models investigated to date. In particular, the fluid-tight container has a specific interior volume such as preferably 3 cubic centimeters for delivering 2 to 3 cc's of a radioactive fluid such as radioactive gas xenon-133 with a specific concentration in a range of 50 to 500 millicuries per cubic centimeter for administering a radiation treatment to the vessel site. For coronary applications, a total dose of 800 to 1000 cGy is preferred.

The foregoing problems are also solved and a technical advance is achieved in an illustrative medical radiation treatment delivery device such as an inflatable balloon catheter for delivering radiation to a treatment site. In particular, the device has a portion such as the inflatable balloon through which radiation from a radioactive fluid such as an isotope of xenon can be radiated therethrough. The balloon normally has a radiation dosimetry unit of measurement such as a radiation dose rate which heretofore had to be calibrated by a physicist or medical radiation expert for providing a prescribed radiation dose within prescribed limits to the patient. This radiation dosimetry unit of measurement is advantageously indicated by the manufacturer and affixed, disposed or positioned on the delivery device as an indicator of the radiation dosimetry unit of measurement.

In one embodiment, the dosimetry unit is simply displayed on or near an end of the device with one or more symbols, letters, or numbers indicative of the dosimetry unit. The indicator can be affixed, disposed, or positioned thereon by printing, photoetching, painting, embossing, raising, or any other method of marking.

In another aspect, the indicator can be a radiation sensitive film which is sensitive to radiation for changing from one visible shade to another. This advantageously can be used to supply information to the attending physician for the purposes of radiation treatment and, in particular, achieved total delivered dose in vivo. Furthermore, this radiation sensitive film can be used either alone or in combination with one or more other dosimetry use indicators to provide the attending physician with a host of information concerning the properties of the catheter or delivery device or the use thereof in patients.

The elongated member of the catheter apparatus comprises at least one of a polyurethane, polyethylene, polyimide, polyvinyl chloride, polyamide, polytetrafluoroethylene, silicone material, or any other similar suitable material. A high density material of at least one of barium, tungsten, lead, tantalum, titanium, bismuth, gold, platinum, palladium, rhodium, or any other similar suitable material is also included in the elongated member to advantageously control the dosimetry unit of the catheter as well as provide radiation shielding for the patient and attending personnel. Similarly, the material of the portion of the delivery device that comes in contact with the treated tissue such as the inflatable balloon(s) advantageously includes at least one of silicone, latex, a synthetic material similar to latex, polyamide, vinyl, polyethylene, polytetrafluoroethylene, polyethylene terephthalate, fluorinated ethylene propylene, or any other similar suitable material. Selection of the balloon material and its density and thickness affect the radiation dosimetry unit of measurement such as the radiation dosage rate. High density materials as previously mentioned, also are advantageously utilized to control the dosimetry unit.

The system of the present invention is useful for the administration of ionizing or other types of therapeutic radiation. The intravascular catheter system of the present invention uses either of several unique radiation carrier fluids. The catheter apparatus preferably includes a plurality of balloon sections, although a single balloon unit can be employed, which is inflatable by an inert radioactive carrier fluid (liquid or gas). Residual blood or other body fluid flows through the artery or tube and possibly the catheter when the balloon sections are deflated and inflated. When the balloon (s) of the several embodiments is inflated, the blood flows through a plurality of sections disposed between and/or within the balloon sections. The system can also be readily modified for tissue or organ-specific design to treat malignancies in passageways or tubes of cancer patients, or even injecting the radio-contents of the catheter into tissue in a limited, controlled manner.

In one embodiment of the present invention, one catheter can perform the two functions of angioplasty as well as the treatment of restenosis, although specific expansion pressures would need to accurately accommodate allowances for tissue dosimetry with respect to balloon thickness, density, materials, etc. The radioactive fluid can initially be used to expand the balloon section, to perform the angioplasty, and then left in situ to prevent or minimize restenosis. Alternatively, the initial expansion for the angioplasty can be performed by introduction of a discrete fluid, which can be removed and replaced by the radioactive fluid. Multiple separate lesions can be treated with the same catheter. As another alternative, the same balloon with radiofluid/xenon gas can be used for synchronous brachytherapy with stent placement.

As a further alternative, the angioplasty catheter can, after it has fulfilled its normal function, be withdrawn and replaced by the catheter apparatus described herein. A lesser number of changes of the catheter is better for the patient, since any intrusion into the body, especially the coronary arteries, can be damaging.

The catheter is designed to be capable of direct insertion into any tumor as well as pseudocavities or defects after surgical or other debulking/resection procedures, or to be maneuverable into a position adjacent to a tumor such as by being maneuverable into a body cavity or along a body passageway through which body fluids will pass. When the catheter is used in a vein or artery, the device can be made to permit the flow of blood within the catheter such as between and/or inside the balloon or balloons or to maintain perfusion flow via the central lumen. Provision is also made for variable balloon(s) thicknesses to provide radiation shielding for the blood and/or redirecting the radiation to the treatment tissue.

Shielding can also be accomplished or effected by an outer shield surrounding the balloon(s). The outer shield can be pulled back proximally to allow the balloon(s) to inflate fully or partially. The proximal end of the outer shield in combination with markings on the proximal end of the catheter are utilized as a dosimetry unit indicator. This is accomplished by varying the volume of the inflatable balloon(s). As the outer shield is pulled back, the length of the balloon(s) that is allowed to inflate increases, thereby increasing the volume of the balloon(s). This, in turn, affects the total radiation dose, radiation dosage rate of the balloon (s), etc. The change in length is calibrated and indicated by the combination of the markings on the proximal end of the catheter and the proximal end out of the outer shield. In addition to being a dosimetry unit(s) indicator, the outer shield also advantageously provides radiation protection to non-treatment site tissue of the patient and to attending personnel.

The balloon section can either comprise a single balloon or a plurality of balloons arranged on the catheter section either peripherally or longitudinally or both. The section is inflated by the radiation fluid that causes the exterior parts of the balloon(s) to improve contact with the tissue to be treated. There can be an exterior inflatable coating of the catheter movable into contact with the tissue. The contact can also be direct between the balloon(s) and the tissue to be treated. The wall of the balloon(s) in the region of the tissue to be treated is of reduced thickness in order to maximize the radiation to the tissue. The thickness obviously must be sufficient to prevent leakage of radiation fluid. The higher the activity, the more important the question of leakage becomes.

The treatment method of the present invention can be applied to a patient either after angioplasty has been performed, or for treating malignant tissue within the brain, lung, esophagus, trachea, cervix, biliary ductal system, colon or rectum, the gastrointestinal system, the gynecological system, on the skin, on ocular structures, head and neck, or other areas accessible to this catheter technology.

The method is designed to apply ionizing radiation prophylactically to post-angioplasty vascular tissue or tumors internal to a patient while minimizing exposure of healthy tissue. Initially, the location and the size of the tissue to be treated are clinically identified, perhaps, with a fluoroscope. The catheter apparatus is then introduced and positioned adjacent to or within the tissue to be treated. The catheter apparatus is then inflated by the radioactive fluid (e.g., gas) thereby exposing the tissue to be treated to radiation. The catheter can include a plurality of discrete balloon sections with special and hypo-dense material, which enable the inflated catheter to match more closely the internal tissue wall, and minimize the amount of gas loss internal to the patient in the event of leakage. The catheter apparatus can include an outer retractable radiation sleeve or shield to prevent the exposure of healthy tissue to radiation. The radiation shield is then retracted to a specific measurable length. Preferably, the radioactive fluid is an inert gas, such as xenon or an isotope of xenon, and emits beta and gamma particles into the tissue to be treated.

A specific coating of integrated and/or layered transitional metal or metal alloy compounds from the surface to the center of the gas-exposed side of the wall of the central catheter lumen, enhances the radiation dose delivered to the targeted tissue. The wall of the lumen attenuates transmission dose to the blood circulating through the hollow inner lumen of the catheter device. Also, the system creates increased by-product radiation, from the impact of beta particles and gamma photons traveling toward the lumen wall. This energy would otherwise be wasted as treatment dose, but instead produces by-product low-energy x-ray photons which increase the deposited energy dose into the target tissue via scattered angle coincidence or secondary redirected x-ray production from the slowing of beta particles traveling into the metal compound on the wall surface. The by-product x-rays travel through the balloon outer wall and deliver useful radiation dose to the targeted tissue (bremsstrahlung).

Another embodiment includes first and second opposing and separate, semi-circular balloons with opposed support displacers attached just proximal and distal to the balloon lengths, upon the outer lumen wall. The built-in injection port unit enables gas-tight redirection of radioactive gas flow from one balloon to the other, one balloon being inflated and delivering treatment dose, while the opposing balloon is deflated. The support displacers are juxtaposed against the vessel wall enabling blood to flow more easily through the space opposite to the treatment side. For a more complete understanding of the catheter system of the present invention, reference is made to the following detailed description and accompanying drawings in which the presently preferred embodiments of the invention are shown by way of example.

As the invention can be embodied in many forms without departing from the spirit of essential characteristics thereof, it is expressly understood that the drawings are for purposes of illustration and description only, and are not intended as a definition of the limits of the invention. Throughout the description, like reference numbers refer to the same component throughout the several views.

BRIEF DESCRIPTION OF THE DRAWING

FIG. 1 is an assembly drawing of the preferred embodiment of medical radiation treatment system of the present invention;

FIG. 2 is a detailed isometric partially sectional view of the deflated catheter apparatus taken along line 2—2 of FIG. 1;

FIG. 3 is a detailed isometric partially sectional view of the fully-inflated catheter apparatus taken along line 3—3 of FIG. 2;

FIG. 11 is an assembly drawing of a fourth embodiment of the catheter system of the present invention with the catheter apparatus being deflated;

FIG. 12 discloses a detailed view of the fully-inflated catheter apparatus of FIG. 11;

FIG. 13 is a detailed partially sectional view of the fully-inflated catheter apparatus taken along line 13—13 of FIG. 12;

FIG. 17 is an isometric view of a fifth embodiment of the present invention disclosing a deflated catheter apparatus for use in treating malignancies in an organ such as the brain, esophagus, lung, or colon;

FIG. 18 is a detailed part sectional view of the inflated catheter apparatus of FIG. 17;

FIG. 19 is a detailed cross-sectional view of the pressure-sensitive flapper valve for the inflated catheter apparatus taken along line 19—19 of FIG. 18;

FIG. 28 is an enlarged, pictorial, proximal end view of the catheter apparatus of FIG. 1 with an alternative embodiment of an indicator thereon;

FIG. 29 is an enlarged, longitudinally sectioned view of the elongated member of the catheter apparatus of FIG. 1 taken along a line through the dosimetry indicator thereof;

FIG. 30 is an enlarged sectional view of an alternative embodiment of the radiation sensitive film of FIG. 28;

FIG. 31 is an enlarged sectional view of another alternative embodiment of the radiation sensitive film of FIG. 28;

FIG. 35 is a pictorial view of a gas-tight container of the present invention having a specific interior volume and concentration of radioactive fluid for administering a radiation treatment to a patient; and FIG. 36 is a pictorial view of the gas-tight container of the medical radiation treatment device of FIG. 1.

DETAILED DESCRIPTION

Figure 4:
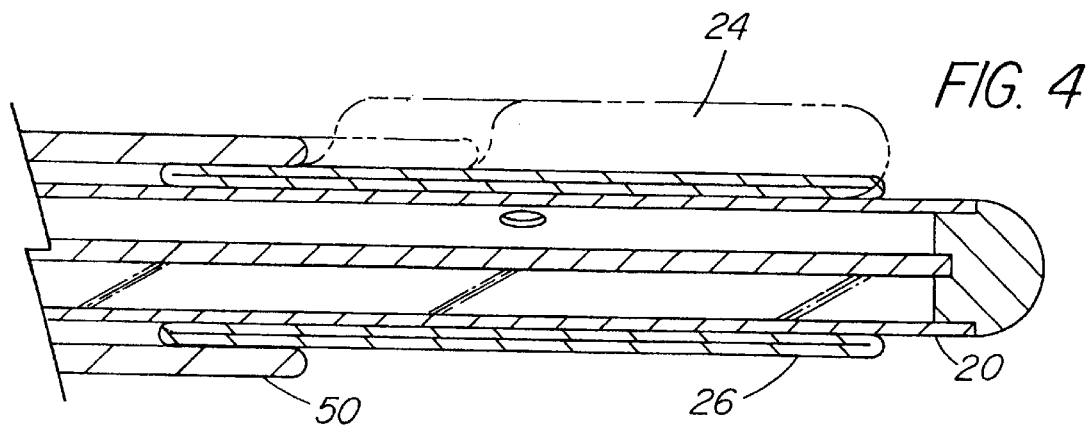
FIG. 4 is a detailed longitudinal sectional view of the deflated catheter apparatus taken along line 4—4 of FIG. 1.
Figure 5:
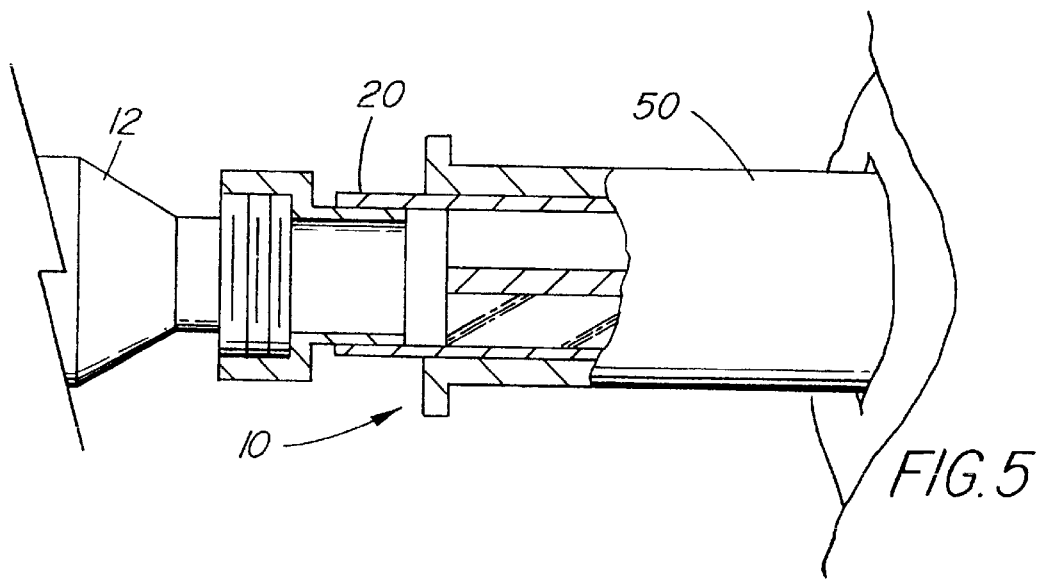
FIG. 5 is an enlarged partially sectional view of the engagement between the protected, syringed gas supply and the catheter apparatus of FIG. 1.

FIGS. 1 to 6 disclose the preferred embodiment of a medical radiation treatment system 10 of the present invention which includes a medical radiation treatment device 14 that is connectable to a radioactive fluid delivery device such as balloon catheter apparatus 20. With reference to FIGS. 35 and 36, medical radiation treatment device 14 includes a sealed source of radioactive fluid, preferably gas 12, which is contained in a sealed, preferably fluid or gas-tight, container 15 illustrated in FIGS. 35 and 36. The gas-tight container 15 in one aspect of the invention is a commercially available, 3 cc, sealed vial with a gas-tight seal membrane 16 at one end thereof for accessing the radioactive gas. The gas-tight seal or membrane is punctured with a piercing cannula or needle so as to permit the radioactive gas in the vial to flow therefrom to the delivery device such as balloon catheter apparatus 20. The fluid or gas-tight container 15 can have an interior volume 17 ranging in size from 0 to 10 cubic centimeters. Preferably interior volume 17 can range from 1 to 7 cubic centimeters. More preferably, interior volume 17 can range from 2 to 6 cubic centimeters and, most preferably, from 2 to 3 cubic centimeters. The particular range of the interior volume is dependent on the size of the particular vessel to be treated which can range from 3 to 8 mm in diameter. This range is intended to serve the coronary, carotid, and other peripheral vessels, and the hepatic visceral vasculature. A-V grafts in the range of 5 to 8 mm are also intended to be included in this grouping. For purposes of treating coronary vessels, a 3 cc vial is selected for containing approximately 2 cc of a radioactive gas including for example, xenon-133. To deliver a prescribed total radiation dose, the radioactive fluid includes a carrier such as carbon dioxide gas or any non-radioactive inert or noble gas and a radioactive substance such as xenon-133 or Xenon-127 or other inert radiogases dispersed in the carrier carbon dioxide gas. The carrier is at least 90% by volume of the radioactive fluid with the radioactive substance being at most 10% by volume of the radioactive fluid. Preferably, the carrier gas is approximately 95% by volume of the radioactive fluid, and the radioactive substance is approximately less than or equal to 5% by total injectable volume of the radioactive fluid. These concentrations and volumes of gas allow a catheter balloon to be inflated to a volume of approximately 0.6 to 1.0 cc generally resulting in relatively low atmospheres of pressure. The radioactive fluid or gas contained in the vial has a specific concentration in the range of 50 to 500 millicuries per cubic centimeter for providing a prescribed dose of radiation to a lesion site for the prevention of restenosis, hyperplasia or smooth muscle cell proliferation. As determined preliminarily from porcine studies, a total radiation dose ranging from 500 to 3000 cGy appears to be an appropriate prescribed dosage. These studies also indicate that a preferred range would include 800 to 1500 cGy. A more preferred total radiation dose would range from 800 to 1000 cGy. To provide such total radiation dose, the specific concentration of the radioactive fluid in the container should range from 50 to 500 millicuries per cubic centimeter, preferably 100 to 150 millicuries per cubic centimeter depending on the anatomical site to be treated such as with the coronaries, the peripheral vasculature, the carotids and other areas such as associated with A-V grafts.

FIG. 35 depicts an enlarged pictorial view of medical radiation treatment device 14 including sealed container 15 with radioactive fluid 12 contained in interior volume 17 thereof. As previously suggested, seal or membrane 16 is disposed at one end of the sealed container, which can be punctured by a piercing cannula or needle. This septum is preferably made of a synthetic rubber, such as Viton® or the like, which minimizes risk of prolonged leakage and/or gas/fluid adherence.

FIG. 36 depicts an enlarged pictorial view of medical radiation treatment device 14 of FIG. 1 including a sealed, gas-tight container 15 with a gas-tight plunger 78 or gas-tight plunger base positioned opposite the distal end thereof for pushing radioactive fluid 12 from interior volume 17 of the container when gas valve 13 is operated to the open position. The gas-tight valve can be a separate component that is attachable to the container or can be integrated into the container. This embodiment of sealed container 15 provides for a much more complete evacuation of the radioactive fluid in interior volume 17. In addition, the container walls can have varying degrees of glass/plastic radiation shielding for alternating higher radiation activity levels.

Intravascular treatment with localized ionizing radiation delivered via conventional solid radio-sourced catheter-based systems has demonstrated a reduction in post-angioplasty neointimal formation in animal models and randomized human clinical trials. Prior art systems can falter with regards to dose homogeneity, optimal efficacy, radiation safety restrictions, patient handling, and radionuclide availability. The present medical radiation treatment system was developed and tested for irradiation with historically safe xenon-133 inert radiogas. In order to determine the efficacy of xenon-133 radiogas to inhibit neointimal formation and subsequent luminal restenosis, angioplasty balloon injury was performed in the coronary arteries of 17 juvenile porcine subjects. Following balloon injury of the coronary arteries of these porcine subjects, 3.0 to 3.5 mm balloons of 30 to 40 mm lengths were positioned to cover and overlap the injured vessel segment. A negative pressure was obtained in the radiocatheter prior to placement. Xenon-133 activity of 250–300 mCi (in 2.0–2.5 cc's) was injected to fill the balloon segment, uniformly abutting the lumen wall. A dose of either 15 Gy or 30 Gy was prescribed and delivered to a target tissue depth of 0.25 mm from the expanded balloon surface. The dwell time during inflation was 2±0.5 minutes (avg.). Prior in vitro dosimetry trials were performed to obtain reference micro-dosimetry results. Summary data analysis including reference tables and graphics, were performed and applied for delivery ranges as described above. This was performed using multiple trials with Cook GRII® balloon catheters of various coronary sizes with different quantities of xenon-133 (millicuries), exposure time (min.), and volumes (cc). Customized solid water phantoms, layered Gafchromic film, laser/light densitometry readings, and referenced dosimetry graphics were standardly applied to obtain these referenced measurements.

Localization of the radiogas filled balloon was verified by Gamma Camera and fluoroscopic imaging. The radiation exposure measured 100 mR/h at the chest wall and 5 mR/h immediately bedside. Two weeks following treatment, the animals were harvested, the arteries perfusion fixed, stained, and morphometrically analyzed. The intimal area (IA) was compared between the irradiated and control arteries. The following results were obtained:

|  | IA (mm$^2$) | P-Value (one way ANOVA test) |
| --- | --- | --- |
| Control (n = 22) | 1.04 ± 0.20 | — |
| Xe-133 15 Gy (n = 9) | 0.34 ± 0.17 | 0.018 |
| Xe-133 30 Gy (n = 8) | 0.38 ± 0.18 | 0.033 |

66% and 44% of the 15 Gy and 30 Gy groups respectively showed IA (mm$^2$) of ≦0.06. A slight trend toward increased thrombosis was noted in the 30 Gy group.

Intimal area (IA) corrected for medical fracture length (IA/FL) was also compared for the harvested vessels:

|  | IA/FL | % absolute ratio reduction |
| --- | --- | --- |
| Control (n = 22) | 0.55 ± 0.06 | — |
| 15 Gy (n = 9) | 0.16 ± 0.08 | 71% |
| 30 Gy (n = 8) | 0.32 ± 0.12 | 45% |

As a result, it was concluded from the harvested vessels that a xenon-133 radiogas balloon catheter is feasible and effective in markedly reducing neointimal formation in the porcine model and can offer a safe and pragmatic modality for clinical use.

The balloon catheter apparatus 20 is preferably of latex or a similar synthetic compound, commonly used for intravascular applications, and void of any silicon-based or other metal-based materials. The balloon catheter apparatus is disposable after each patient use, and is designed to handle peak expected pressures less than those used in conventional angioplasty. These pressures typically range from one to ten atmospheres.

As used herein, the term "fluid" includes any gas, liquid, or gel-type substance that generally conforms to the shape of the container within which it is held, and is fluent. While the catheter apparatus of the present invention is used in conjunction with a radioactive carrier fluid, it is preferred that the fluid is a gas, and for reasons hereinafter set forth, an inert gas, such as preferably xenon, or an isotope of xenon. However, the present invention is not limited to xenon gas or an isotope thereof, and the preferred fluid includes all gases and isotopes thereof, radioactive gases or radiogases (inert and/or non-inert) or gases capable of fluorescence, phosphorescence, or luminescence (electron stimulation). Examples of gases include, but are not limited to, xenon, krypton, neon, radon and their isotopes. A radiogas can be dissolved in a liquid or solution (sterile) such as sterile water or saline and be used as a liquid radiofluid. Liquids include all isotopes of liquids and solutions. An isotope can be radioactive or non-radioactive. Radioactive includes nuclear (nucleus) decay of an atom. A radionuclide is any radioactive atom. Fluorescence, phosphorescence or luminescence is associated with electron instability and subsequent emission of radiant energy. Liquids also include all gases dissolved in liquids or solutions. Examples of liquids include, but are not limited to, liquid phosphorus, rhenium, yttrium, technetium, iodine, gallium, chromium, strontium, thallium, samarium, ytterbium, palladium, and all isotopes thereof, and all compounding and binding solutions thereof. All gels utilizing the aforementioned gases or liquids (solutions) are also contemplated. Additional radionuclides can include osmium, vanadium, ruthenium, bismuth, or other transitional heavy metals and their isotopes for liquid and/or gel-type compounding. All inert dual photon/electron emitting radionuclides are further contemplated as well as all inert single particle radio-emitting nuclides and all non-inert radionuclides thereof. Still further contemplated are all inert or non-inert radiofluids which use electron stimulation to produce by-product fluorescent, phosphorescent or luminescent radiant energy for patient treatment. The use of by-product radiant energy emissions including fluorescent, phosphorescent or luminescent emissions can be utilized for therapeutic treatment. Implementation of radionuclide and by-product radiant energy emissions can be applied by the use of the catheter apparatus in the following combinations;

(a) gases and/or fluids or single fluids alone either as a gas-gas or gas-liquid, and/or either inert or non-inert, and/or radioactive or non-radioactive such that the photon or electron emissions of one radiofluid can induce electron shift, scatter, or a quantum level change in the electron shell of the same or other combined "fluid" atoms thereby causing production of relatively low energy photon/electron (possibly in a cascaded amplification) emissions into the targeted tissue as a controlled/calculated dose;

(b) radiofluid(s) as described in (a), except that induction of listed radiant energy is provided via electrical source stimulation from an electrode, cathode, wire or other transmission source such that controlled electrical currents and/or electrical potential delivered through the catheter to the radiofluid or non-radiofluid of the balloon catheter which causes expected electron excitation and/or quantum level fluctuations with by-product fluorescence, phosphorescence and/or luminescence for the aforementioned therapeutic treatments; and (c) phosphorus and/or other known fluorescent metals or alloys are implanted in the balloon material and/or catheter structure so that the combinations described in (a) and (b); (i.e., radioemission, by-product decay energy and/or direct electrical stimulation) can cause effect on the implanted/layered materials so as to create fluorescent, phosphorescent or luminescent energy delivery as these materials stabilize their electron structure after such stimulation.

Figure 6:
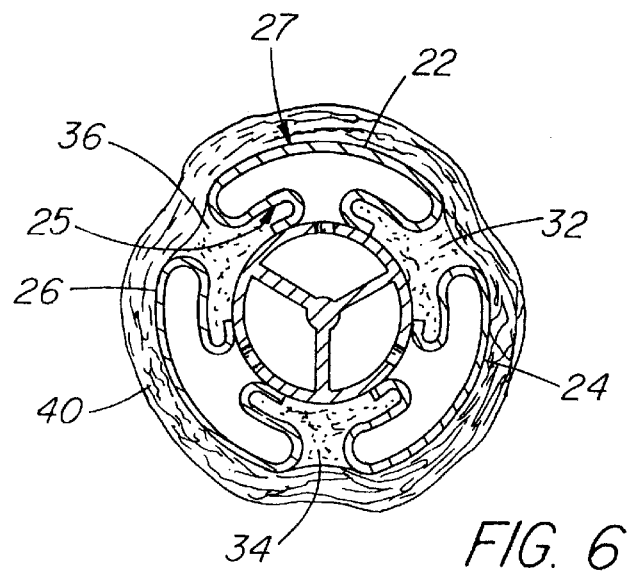
FIG. 6 is a detail cross-sectional view of the fully-inflated catheter apparatus as shown in FIG. 1 inside an arterial wall.

The unique medical radiation treatment delivery system 10 of the present invention uses a radioactive fluid. The catheter apparatus 20 includes at least a single balloon and, preferably, a plurality of balloon sections 22, 24 and 26, which are inflated with the radioactive fluid. As is seen in FIG. 6 residual blood flows through the vessel when the balloon or balloon sections 22, 24, and 26 are inflated through a plurality of interposed sections 32, 34, and 36 disposed between the balloon sections.

Figure 25:
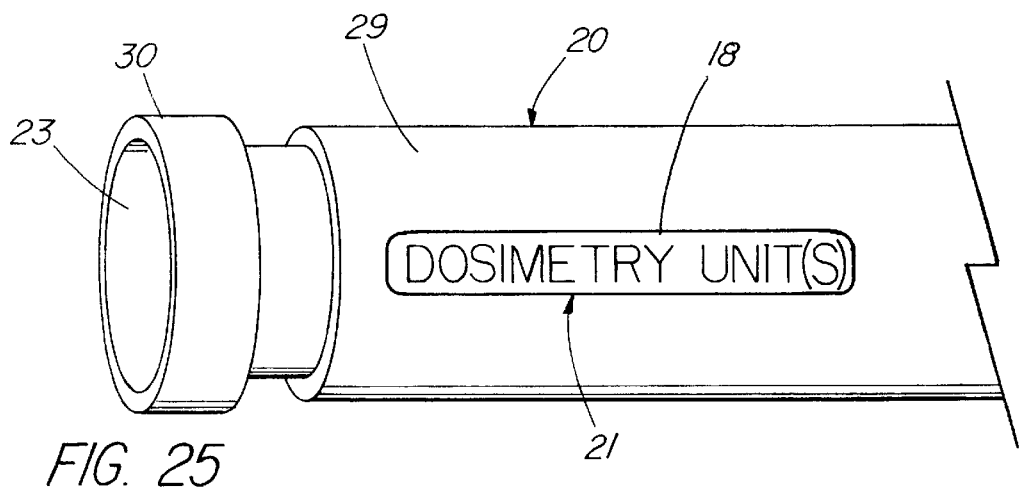
FIG. 25 is an enlarged, pictorial, proximal end view of the catheter apparatus of FIG. 1 with a radiation dosimetry unit(s) indicated thereon.

FIG. 25 depicts an enlarged, pictorial, proximal end view of a medical fluid delivery device such as catheter apparatus 20 of FIG. 1. Affixed, positioned, disposed, or connected to, on, or about the outer surface of catheter apparatus 20 near the distal end thereof is indicator 21, which is indicative of a radiation dosimetry unit of measurement 18. By way of example, radiation dosimetry unit of measurement is at least indicative of the radiation that can be radiated through at least one portion of the catheter apparatus. The at least one portion of the catheter apparatus includes a single balloon or, preferably, balloon sections 22, 24 and 26, which are inflated with a radioactive fluid. The radiation dosimetry unit of measurement for the balloon or balloon sections of the catheter apparatus can include, but is not limited to, radiation dose rate, total radiation dose at a predetermined tissue depth, radiation source activity, radiation time exposure, tissue depth of a radiation dose, radiation source, or an incidental radiation dose rate. The total radiation dose at a reference tissue depth for a radioactive fluid delivery device such as catheter apparatus device 20 is approximately equal to the radiation source activity (i.e., specific activity in millicuries per volume or density unit) multiplied by the radiation dose rate of the device multiplied by the exposure time of the radioactive fluid source. By way of example, a typical prescribed total radiation dose for a radiation delivery device such as catheter apparatus 20 can be 1400 cGy. This total radiation dose rate is referenced to a tissue depth at a delivery interface of typically 0.25 mm or 0.50 mm for a radioactive fluid such as xenon-133 gas. A typical radiation dose rate for a balloon catheter of the present invention can typically be in the range of 2 to 10 cGy per minute per millicurie (mCi).

The radiation dose rate of a balloon material is a function of or is dependent upon the thickness of the balloon material, the density of the balloon material, and/or the volume of the balloon. In addition, the volume is, in turn, dependent upon the length of the radiation source and, in particular, the longitudinal length of the balloon along with the diameter and radius of the balloon. The axial length of the balloon is important with respect to the radiation source in that accumulative dosimetry effects (scatter, coincidence, photo electric) are achieved with the radioactive fluid disposed along the length of the catheter. The radiation dose rate is also affected by the surface area of the inflatable balloon in response to the radioactive fluid.

Radiation source activity is a function of the radioactive fluid or preferably of the radioactive gas that is used with the radiation treatment. As described hereinafter, radioactive xenon-133 gas is preferred in that it is an inert gas that provides synchronous gamma and beta radiation emission with a half life of approximately five days. Concentrations of xenon-133 gas can typically range from 10 mCi to 150 mCi per cc or more of gas volume at the time of calibration.

Radiation exposure time is prescribed by the attending physician, commonly with a speciality in radiation oncology, nuclear medicine or nuclear oncology. Exposure times range from less than a minute upwards to ten minutes, depending on the activity of the radiation source. Particular concentrations of the radiation source are normally provided with commercially available radiation sources. These concentrations are used by the physician to determine radiation exposure time. The radiation dose rate is a function of the properties of delivery devices such as catheter apparatus 20, which in turn is a function of balloon material thickness, density and volume as previously indicated. An external or internal brachytherapy medical radiation delivery device can be experimentally dose calibrated and verified by a radiation physician specialist, medical physicist, or certified radio/nuclear laboratory, or with approved device-specific computer software for patient treatment. With such a calibrated radiation dose rate, the physician can calculate and prescribe the required radiation source concentrations and exposure times for treatment of the patient. The calibration of the delivery device typically includes positioning the delivery device in a phantom and positioning radiation detectors/sensors at a prescribed distance away from the delivery device in the phantom. A series of measurements are used to graph the radiation from a series of radioactive fluid concentrations applied thereto. Such calibration is necessary and demanded by various regulatory agencies so that the radiation treatment provided to a patient is within specified limits of the prescribed total radiation dose. In addition, multiple radiation safety profiles are evaluated for handling and delivery.

Figure 26:
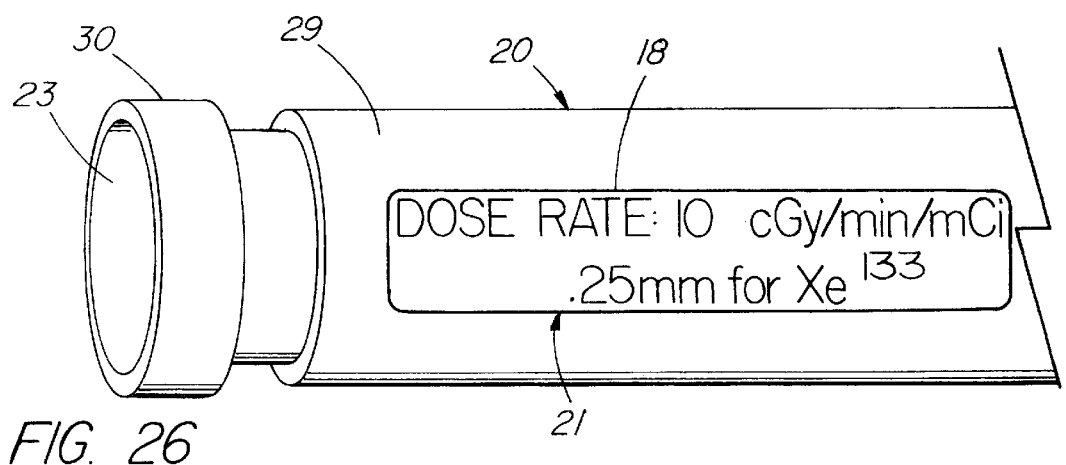
FIG. 26 is an enlarged, pictorial, proximal end view of the catheter apparatus of FIG. 1 with a radiation dose rate indicated thereon.

FIG. 26 depicts an enlarged, pictorial, proximal end view of catheter apparatus 20 of FIG. 1. In this particular embodiment, the radiation dosimetry unit of measurement is the radiation dose rate, which is indicated as 10 cGy/min/mCi at a tissue depth of 0.25 mm for a radiation source of xenon-133. With this radiation dosimetry unit of measurement indicated on the catheter, an attending physician can readily calculate and prescribe a desired total radiation dose for a patient with commercially available radiation concentrations of, for example, xenon-133 and a calculated radiation exposure time as a verified standard for a particular catheter/balloon make, style, and size. As a result, the attending physician eliminates the need to perform more laborious calculations and independent measurements, or having the delivery device sent to a medical physicist or laboratory for calibration of the radiation dose rate of the delivery device.

In addition, the catheter is made in a uniform-single construct with a gas-tight injection port component, which is leak-proof and injection "friendly" and has a septum of "resistant" synthetic rubber (Viton), which minimizes risk of leak or xenon adsorption. Furthermore, a leak-tight directional valve controls and locks direction of radiofluid passage for safety. A standard-type catheter would not provide this.

Although the indicator is affixed, positioned, disposed, connected to, on, or about the proximal end of the catheter for visualization by the attending physician, this indicator 21 is normally indicative of the portion of the delivery device such as the inflated balloon of a balloon catheter, which is inflated for the purposes of making contact with tissue to be treated. More particularly, the indicator and the radiation dose rate is indicative of the material that comes in contact with the tissue to be treated. By way of example, the outer surface or wall of the balloon catheter along with the density and thickness thereof are one of the major factors in determining the radiation dose rate. This radiation dosimetry unit of measurement is experimentally calculated or computer modeled and verified with experimental calculations and applied to the proximal end of the delivery device. The indicator of the dosimetry unit can be printed or painted on the outer surface of the catheter, embossed in or raised from the outer surface of the delivery device. The indicator can comprise at least one of a plurality of symbols, letters or numbers disposed on the radioactive delivery device for indicating the dosimetry unit of measurement. It is also contemplated that any indicator of whatever type can be affixed, disposed or positioned on the delivery device for the purposes of indicating at least one radiation dosimetry unit of measurement. Not only can the radiation dosimetry unit of measurement be directed to the portion of the delivery device that comes in contact with the tissue to be treated, but also radiation indicators such as incidental radiation dose rate, which is important to attending personnel to minimize their exposure to radiation.

Figure 27:
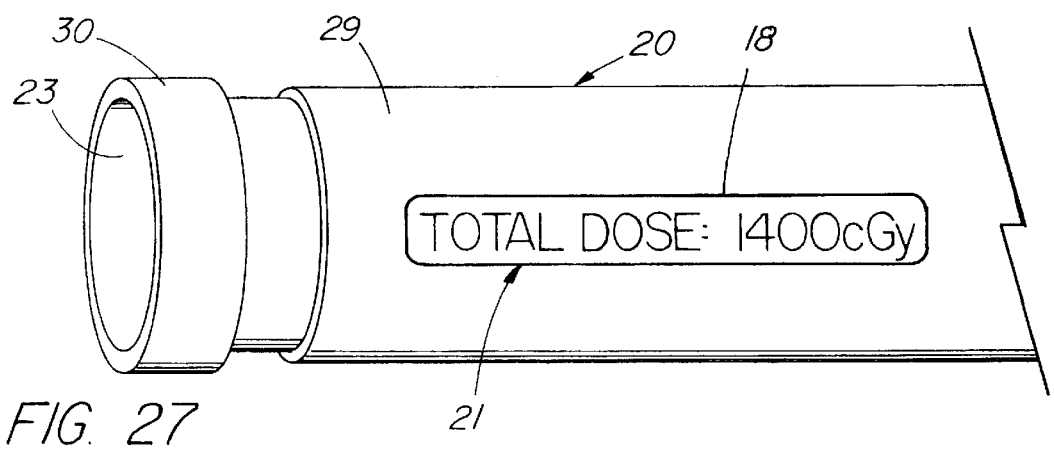
FIG. 27 is an enlarged, pictorial, proximal end view of the catheter apparatus of FIG. 1 with a total radiation dose indicated thereon.

FIG. 27 depicts an enlarged, pictorial, proximal end view of catheter apparatus 20 of FIG. 1 in which the radiation dosimetry unit of measurement is indicated as total dose and, in particular, a total radiation dose of, for example, 1400 cGy. This indicator 21 is thus printed, embossed, or raised and indicated as total dose. Inflation lumen 23 extends longitudinally through elongated member 29 of catheter apparatus 20. A gas tight fitting/hub 30 is affixed in a well-known manner to elongated member 29 of catheter apparatus 20. These particular components of catheter apparatus 20 are also depicted in FIGS. 25 and 26. Elongated member 29 comprises a polyurethane, polyethylene, polyimide, polyvinyl chloride, polyamide, polytetrafluoroethylene, silicone, or any other suitable material. The selection of the catheter material is typically dependent on the particular anatomical site that the catheter apparatus is to be positioned or extended through. These elongated member materials can also be coated with a hydrophilic slip coating to further ease insertion and introduction to the treatment site. In addition to well-known hydrophilic slip coatings, the inner and/or outer surfaces of the elongated member can be treated such as with ion beam bombardment or deposition, which is commercially available from the Spire Corporation, Bedford, Mass. Ion beam bombardment or deposition can significantly alter the surface energy density of the elongated member material to reduce adhesion of thrombus or other agents thereon. This treatment is also known to provide an antibacterial, antifungal, or an antithrombogenic surface.

To minimize radiation exposure to attending personnel, elongated member 29 of catheter apparatus 20 can include a high density material to absorb and/or block the radiation from the radioactive fluid when in inflation lumen 23. By way of example, this high density material can constitute a loading of greater than 30 percent by weight of, for example, barium, tungsten, lead, tantalum, titanium, bismuth, gold, platinum, palladium or rhodium.

Referring the reader's attention to FIGS. 1–4 and 6–8, the portion of the delivery device such as balloon 22 through which radiation from a radioactive fluid is normally directed includes at least one of silicone, latex, a synthetic material similar to latex, polyamide, vinyl, polyethylene, polytetrafluoroethylene, polyethylene terephthalate, fluorinated ethylene propylene, or any other suitable material. The balloon material can also include a loading of high density material to absorb or block radiation and thereby consequentially redirect the radiation to the treatment site. This material can also block or lessen radiation exposure of blood passing through the balloon sections. This high density material can be a loading of greater than 20 percent by weight of at least one of barium, tungsten, lead, tantalum, titanium, bismuth, gold, platinum, palladium or rhodium. The radiation dose rate of the balloon can also be altered or redirected by applying a thin coating of a metal or other reflecting materials to the various inner and outer surfaces of the balloon as herein later described.

FIG. 28 depicts an enlarged, pictorial, proximal end view of catheter apparatus 20 of FIG. 1 with an alternative embodiment of indicator 21 affixed, disposed or positioned thereon. Indicator 21 includes a housing or holder 19 as depicted in which a radiation sensitive film 31 is positioned therein. The arrow indicates the placement of radiation sensitive film 31 into indicator holder 19. Positioned adjacent to aperture 33 on the indicator is a visible shades scale 35 having various shades of gray between white and black at the opposite ends thereof. When exposed to various dosages of radiation, radiation sensitive film 31, such as a Gafchromic type film from, for example, Nuclear Associates of Carle Place, N.Y., changes color. The Nuclear Associates' Gafchromic film exhibits various hues of blue in response to radiation. This change in color is visible as a change from clear to black with various shades of gray therebetween. The various shades of gray or blue indicate the amount of radiation film 31 has been exposed to. Thus, the attending physician can readily match the visible shade of radiation sensitive film 31 with gray scale 35 to determine the radiation dose and activity of the radiation source. For purposes of convenience, total dose amounts can be printed or indicated right next to each shade of gray on gray scale 35.

FIG. 29 depicts an enlarged longitudinal sectioning of elongated member 29 of catheter apparatus 20 through indicator 21. Radiation sensitive film 31 is inserted into channel 37 of the indicator for visual reading of the change in color of the film. The bottom material 39 of indicator 21 is preferably selected to be that of the material coming in contact with the tissue to be treated. Even more preferably, the bottom material is selected to be of equal thickness along with the same loading of the high density material of the balloon material. This is to best approximate the radiation dose being applied through the balloon to the treatment site. Depending on the radiation volume size, the thickness and loading of the bottom material can be modified to more closely approximate the total radiation dosage being radiated at the treatment site.

FIG. 30 depicts an enlarged sectional view of an alternative embodiment of radiation sensitive film 31. In this embodiment, the radiation sensitive film is layered in a stair step configuration to provide a greater change in color or the gray scale depending on the type of radiation source being utilized.

FIG. 31 depicts still another alternative embodiment of radiation sensitive film 31 in which strips of radiation sensitive Gafchromic type film are butted end-to-end. Each strip or segment has a different sensitivity to radiation and thus can be utilized to indicate a much larger range of radiation doses being exposed thereto.

Figure 33:
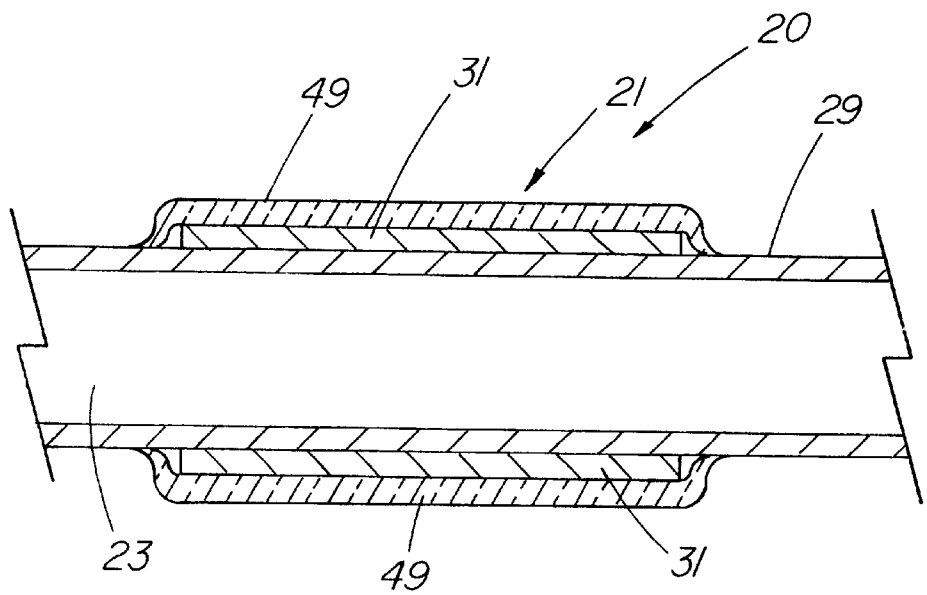
FIG. 33 is an enlarged, longitudinally sectioned, proximal end view of the catheter apparatus of FIG. 1 with still another alternative embodiment of an indicator thereon.

FIG. 33 depicts an enlarged, sectioned, proximal end view of catheter apparatus 20 of FIG. 1 with still another alternative embodiment of radiation indicator 21 thereon. In this particular embodiment, radiation indicator 21 includes radiation sensitive film 31 positioned around elongated member 29 of the catheter. The thickness of elongated member 29 underneath radiation sensitive film 31 is formed to approximate the relative thickness of the balloon catheter as well as the treatment depth of the tissue intended to be in contact with the balloon. As a result, the wall thickness of member 29 beneath radiation sensitive film 31 best approximates the balloon material and tissue so that the radiation sensed by film 31 is that at the desired tissue treatment depth. The xenon radioactive gas resides in inflation lumen 23 of the elongated member as well as the inflatable balloon. Positioned over and around radiation sensitive film 31 is transparent material 49 such as clear silicone so as to hold the radiation sensitive film in position around the proximal end of the catheter apparatus. The clear transparent property of this material or other similar materials provides for minimal distortion of the hue or color of the radiation sensitive film.

Figure 34:
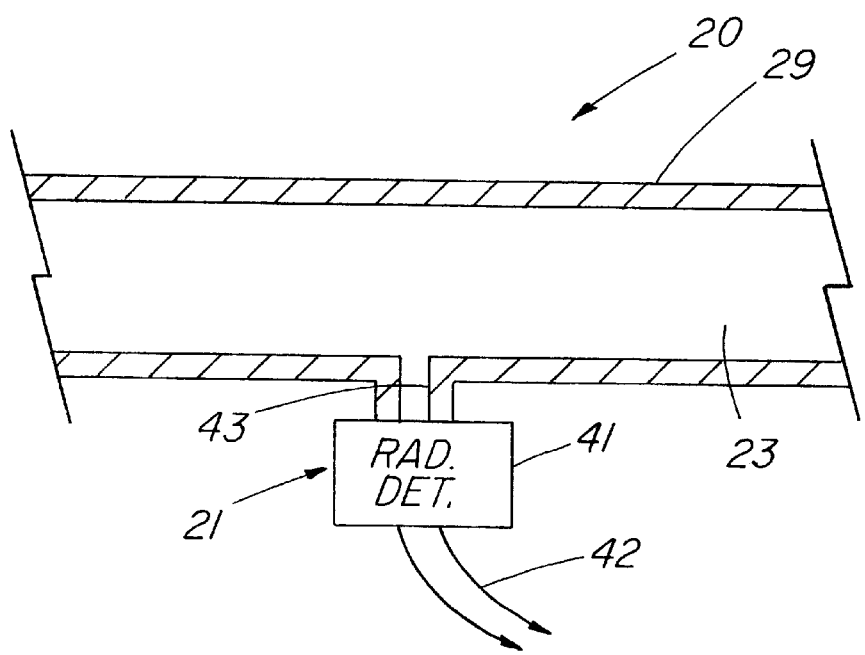
FIG. 34 is an enlarged, longitudinally sectioned, proximal end view of the catheter apparatus of FIG. 1 with yet still another alternative embodiment of an indicator thereon.

FIG. 34 depicts an enlarged, sectioned, proximal end view of the catheter apparatus 20 of FIG. 1 with yet still another embodiment of indicator 21 disposed thereon. In this particular embodiment, the radioactive fluid not only passes through inflation lumen 23 of elongated member 29 but also out of side port 43 to electronic radiation detector 41. This electronic radiation detector is commercially available and is an electronic ion exchange detector. Electrical conductor leads 42 extending from the radiation detector are connected to an electronic display unit such as an LCD or LED display for displaying radiation level(s).

Figure 32:
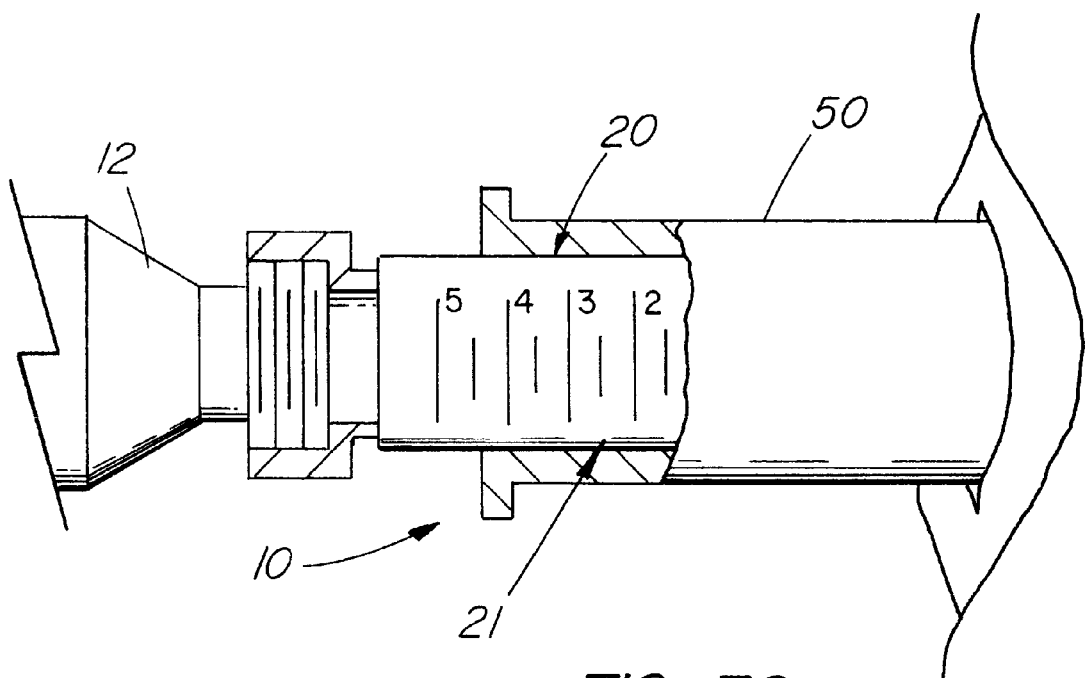
FIG. 32 is an enlarged, partially sectioned view of the catheter apparatus of FIG. 1 with a dosimetry unit indicator thereon.

Returning the reader's attention to FIGS. 1–6, the method of the present invention is designed to apply ionizing radiation prophylactically to post-angioplasty vascular tissue or tumors disposed internally within a patient while minimizing exposure of healthy tissue. Initially, the location and the size of the lesion 40 to be treated are clinically identified, perhaps, with a fluoroscope. The catheter apparatus 20 is then introduced and positioned adjacent to the lesion 40. The plurality of discrete balloon sections 22, 24, and 26 of a special, hypo-dense, thin material enable the inflated catheter apparatus 20 to more closely match the internal tissue wall, and minimize the amount of internal gas loss in the event of leakage. The catheter apparatus 20 includes an outer retractable radiation sleeve or shield 50 to prevent the exposure of healthy tissue adjacent to the lesion to radiation. After the catheter apparatus 20 is positioned alongside the lesion 40, the radiation shield 50 is retracted to a specific measurable length as depicted in FIG. 32. This specific length controls dosage rate and radiation source volume size. The balloon sections 22, 24, and 26 are then inflated with the radioactive fluid exposing the lesion 40 to the radiation dosage. The preferred gas, xenon or xenon isotope, emits beta and gamma particles into the lesion 40. Furthermore, indicator 21 can be used to establish dosage rate and total radiation dose.

Figure 7:
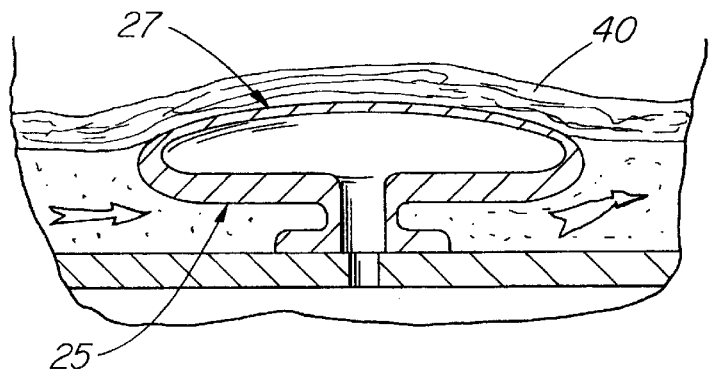
FIG. 7 is a second embodiment disclosing a detailed sectional view of a balloon of a catheter apparatus being fully-inflated and having a thickened interior wall and a thinner, hypo-dense outer wall.
Figure 8:
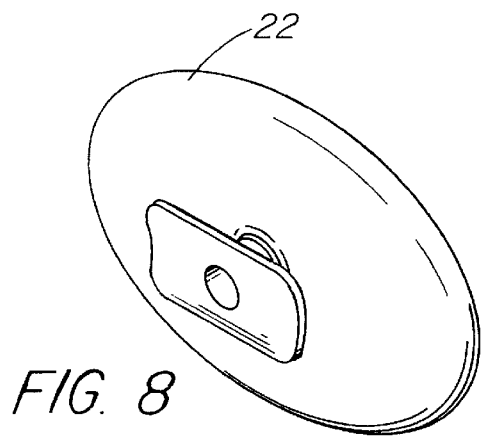
FIG. 8 discloses a detail of an inflated balloon of the catheter apparatus shown in FIG. 7.

The catheter apparatus 20 enables substantial blood or other fluid flow between the balloon sections 22, 24, and 26 when fully inflated. The balloons sections 22, 24, and 26 include a unique inner and outer surface 25 and 27 configuration. The radiation flow is directed through the outer surface 27 of the catheter apparatus 20 to the lesion 40 while exposure to radiation of the blood flowing internal to the catheter apparatus 20 is minimized. Accordingly, the inner surface 25 is more attenuating to the transmission of radiation than the outer surface 27. Either the inner surface (wall) 25 is thicker than the outer surface (wall) 27 as shown in FIG. 7, or the inner surface 25 includes a layer of material that is resistant to the penetration of radiation (not shown).

Figure 9:
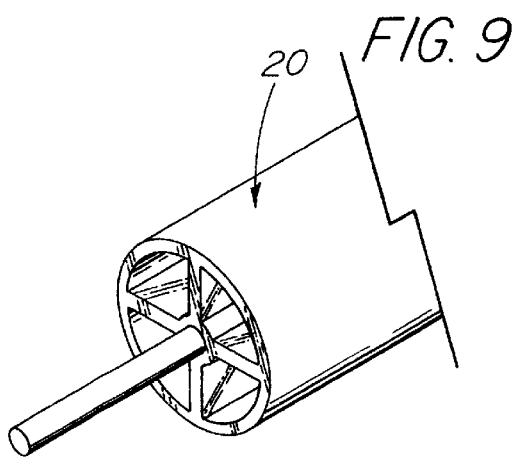
FIG. 9 discloses a third embodiment of the catheter apparatus having a removable central lumen guide/localizing wire that is radio-opaque.
Figure 10:
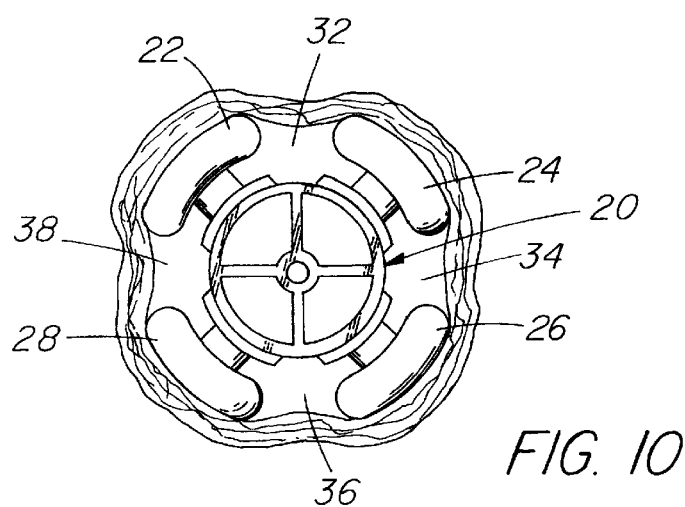
FIG. 10 is a detail cross-sectional view of the fully-inflated catheter apparatus of FIG. 9 within the arterial wall.
Figure 14:
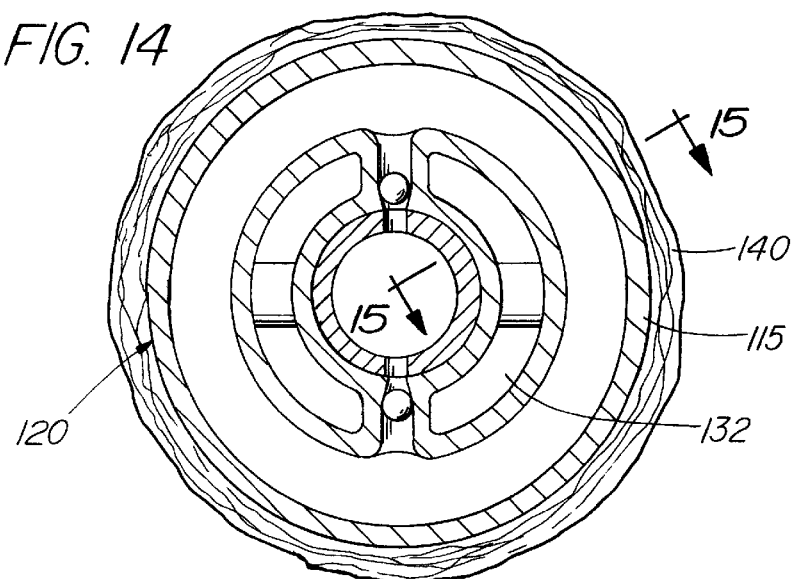
FIG. 14 is a detailed cross-sectional view of the fully-inflated catheter apparatus of FIG. 11.
Figure 15:
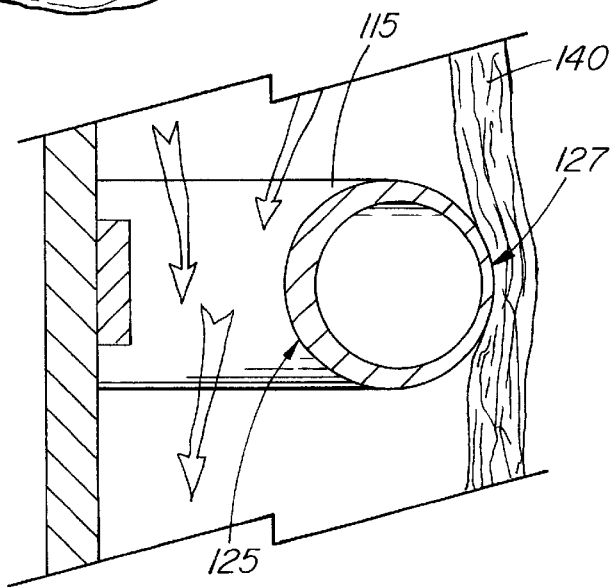
FIG. 15 is an exploded sectional view of a fully-inflated balloon of the catheter apparatus of FIG. 14, the balloon having a thickened inner wall and a thinner hypo-dense outer wall.

Preferably, either three discrete balloon sections are used as shown in FIGS. 1 through 6, or four balloon sections 22, 24, 26, and 28 with interposed sections 32, 34, 36, and 38 can be used as shown in FIGS. 9 and 10.

One primary application of the system of the present invention is for use after standard, angioplasty procedure: including multiple lesions at one treatment session. Controlled internal radiation therapy is provided to an artery or vessel for the prevention of arterial restenosis due to smooth muscle hyperplasia or similar related pathology. This will enable cannulation via the same access port from the pre-emptive dilatation procedure.

Discrete balloon sections or segmented systems 22, 24, and 26 or possible variants thereof are specifically structured to enable the application of a radioactive gas for therapeutic intent.

FIGS. 11 through 16 disclose another embodiment of catheter apparatus 120 of the present radiation delivery device invention. Drafted segmental and peripheral "tire-like" balloon sections or segment configurations 115 optimize direct circumferential abutment of the entire lumen wall at 127. This will minimize intraluminal attenuation factors and maximize homogeneous dose rate delivery, conforming and enabling irregularly-shaped intimal surfaces. Also, when the catheter segments 115 are pressurized and expanded, a significant residual rate of intraluminal blood flow is enabled internal to the segments, through aperture 132 as indicated at inwardly facing surface 125 of balloon section 115.

The catheter apparatus of the present invention is designed to minimize the secondary risk of medical complications caused by blood flow deficiency due to underlying disease or vasospasm in the peripheral, kidney, and, particularly, the heart vessels. The centrally directed perfusion flow can also contribute to outwardly directed pressure gradients, therefore, further supporting and stabilizing the radioactive-gas expander balloons against the arterial wall.

The catheter apparatus of the present invention enables individual patient flexibility as to dosage, treatment exposure time, and lesion segment lengths. Also, since blood flow cannot be completely occluded during therapy, radiation time need not be limited to less than three minutes, and therefore, very high energy gamma emitters or radiation activity levels are not needed. More expensive loading devices, shielded treatment rooms, and solid radio sources are thereby avoided. Also, healthy tissue is not unnecessarily exposed to passing or placement-preparation time irradiation as with other solid-source systems.

If inadequate blood flow rates or distal symptoms occur, this closed, sealed and inert radioactive gas system 10, 110 can be easily deflated without exposing the patient or medical personnel to real radiation risk. After flexibly allowing for several minutes of reperfusion time, the catheter apparatus 20, 120 can be simply reinflated and the prescribed treatment time/dose (several times if needed) is resumed without diminishing the therapeutic benefit.

Furthermore, the system of the present invention enables the treating therapeutic radiologist to address more than one vessel system or lesion even distal to the distribution of the primary lesion that may require subjective variation in post-dilatation balloon length and diameter due to sensitivity of distal ischemic-prone tissue from risk of prolonged diminished blood flow.

The sectioned, segmented or compartmentalized radioactive gas delivery tracks communicating with the end point expander balloons, will minimize the potential volume of gas leak should a balloon lose integrity. The residual catheter gas volume may be withdrawn into the shielded syringe without further leakage. The bloodstream released gas poses no real radiation or chemical threat to the patient, because of the physical and biological properties of the inert gas.

Figure 16:
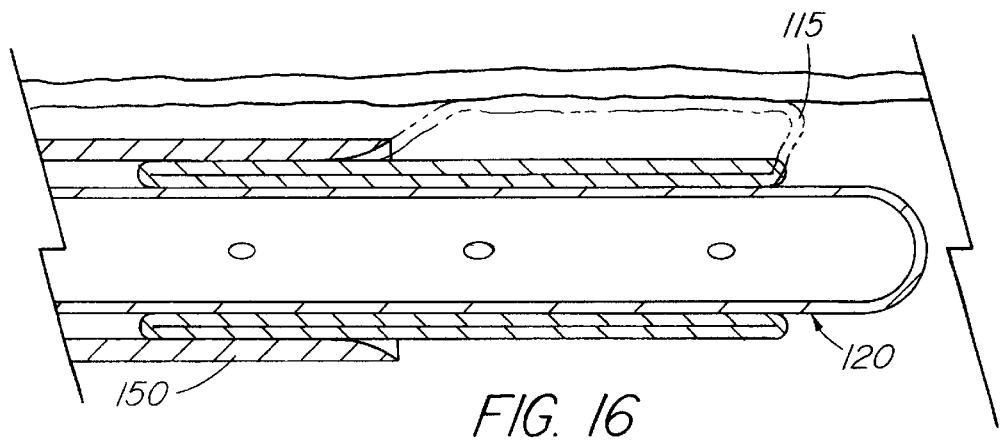
FIG. 16 is a detailed sectional view of the partially-inflated catheter apparatus of FIG. 11, complete with the retractable sleeve.

The length of the distal expandable component of the catheter apparatus 20 or 120 is covered by a thin, retroslidable or static sleeve 50 or 150, as shown in FIGS. 4 and 16, which is radiopaque for purposes of imaging localization. The sleeve 50 or 150 is in direct continuity with and manipulatable externally by the physician. The sleeve is positioned proximal to the access port to the balloon sections or segments. After confirmation of placement of the distal catheter apparatus 20 or 120 by fluoroscopic means, the catheter sleeve 50 or 150 is slowly pulled back, and a concordant ruler is exposed in parallel, measured in millimeters, whereby the treating physician accurately determines the length of the balloon to be expanded, and the length of the vessel wall to be treated 40 or 140. Alternatively and preferably, indicator 21 can be utilized to establish selectively the dosage rate as illustrated in FIG. 32. This will enable immediate confirmatory calculations as to specific dose rates, treatment time, and the volume of the radioactive gas injected.

The proposed radioactive gas or gases emit gamma photons enabling imaging and semi-log calculations to be performed at bedside using a conventional gamma camera and computer (not shown), which is left on the monitor distal to the treatment field to detect any early leakage for concerned physicians at minimal additional cost.

Although the lumen diameter is narrow and contains only a small fraction of the total volume of radioactive gas injected per session, the designed shielding properties of the sleeve 50 or 150 or outer lumen wall layer minimize any significant normal tissue or blood cell exposure over the remaining non-inflated catheter length, particularly with the energies of emission of the isotopes selected.

The interval and possibly staggered placement design of the entry portals and columns between the catheter body and expansion "modules" or balloons enable cutoff control of the balloon expansion length due to the controlled length of outer sleeve retraction.

The primary rationale and benefits for the therapeutic application of radioactive xenon gas with the "ASP" or similar catheters for intravascular brachytherapy enable precise determination of total dose, dose rate, and depth distribution of radiation emitted from a source.

Radioactive xenon-133 gas, and less commonly used xenon-127 gas and krypton 85, as well as, technetium compounds, have been widely used for several years and proven relatively safe within medically accepted radiation levels for nuclear diagnostic studies involving the lung and the measurement of blood and fluid flow rates through vessels to specific organs. When used as an unsealed free-gas form, the inert, noble gas properties essentially enable the molecules to rapidly dissipate throughout the body of the patient or through a room, without any prolonged organ accumulation or interaction within specific dose ranges. Rapid expulsion of the relatively lower energy nuclear emissions of the xenon, is quickly re-released from the bloodstream through the lungs.

Xenon is a very stable element which can be pressurized, stored, and made to high millicurie activity per cubic centimeter (cc) with very reasonable cost and availability.

Xenon-133 provides both a beta particle (101 keV avg.; 364 keV max.), and at least two usable photons (32 kev 48 percent; 81 kev 37 percent).

The beta particles offer excellent initial dose rate delivery when directly adjacent to the tissue with the first millimeter. The particle does not penetrate much beyond the first millimeter of tissue, thereby not contributing to any significant distal normal tissue exposure.

The gamma photon energies and their decay fractions provide complementary dose deposition for the first millimeter, and primary dose delivery for an additional several millimeters of arterial wall and adjacent tissue. The high percent of attenuated, and lower energy photons beyond this point provide for ease of personnel protection with routine lead jackets, or by placing a cover over the external surface of the treated region. Furthermore, the sensitivity of a small field gamma camera provides simple image monitoring and dose evaluation simultaneously.

Xenon-133 is commercially available within a week in concentration ranges from 10 mCi to 150 mCi per cc or more of gas volume. Also, the cost is currently estimated to be less than a few hundred dollars a dose of 150 mCi. A single dose order can be used to treat several patients per day for a full week, as the physical half-life is 5.2 days. Also, no special equipment, storage, or delivery devices are necessary, except for routine facilities available in most nuclear medicine or radiation oncology departments.

In vivo and in vitro facilities with standard exhaust hoods or negative pressure rooms provide adequate protection for this sealed use of xenon gas. A metered dose can safely and readily be transported to nearly any treatment site by one person, and administered by one person without special radiation protection needs, such as is necessary with higher energy photon sources for conventional brachytherapy. The most expensive addition to a standard treatment room is a simple negative pressure ventilation system, as a backup safety mechanism.

Selective balloon shapes and designs with various thicknesses and pliable lucent and radio penetrable materials enable site specific, intracavity or intraparenchymal insertion and localization from external origin and placement. FIGS. 17, 18, and 19 illustrate various other applications for catheter apparatus 220 which can include brain, lung, esophagus, trachea, cervix, biliary ductal system, colon or rectum, the gastrointestinal system, the gynecological system, and head and neck. Balloon 215 is shown mounted on the distal end of catheter apparatus 220, where the catheter lumen comprises the inflation lumen for balloon 215 and includes a valve. All can optimize the self-introduction of radioactive Xenon-133 or others, with controlled expansion and dose rate delivery while enabling individual tissue compliance such that the entire tissue is immediately and homogeneously adjacent to this high or low dose rate source without requiring surgical implant disruption, patient isolation, use of high energy concentrations of other radionuclides, patient or medical personnel risk from leakage, expensive materials, or costly radio-safe suite facilities.

The compliance, stress, and thickness properties of the balloons enable adequate and complete volume expansion against the variable surface of the arterial wall at less pressure than conventional therapeutic dilation plasty catheters.

Figure 20:
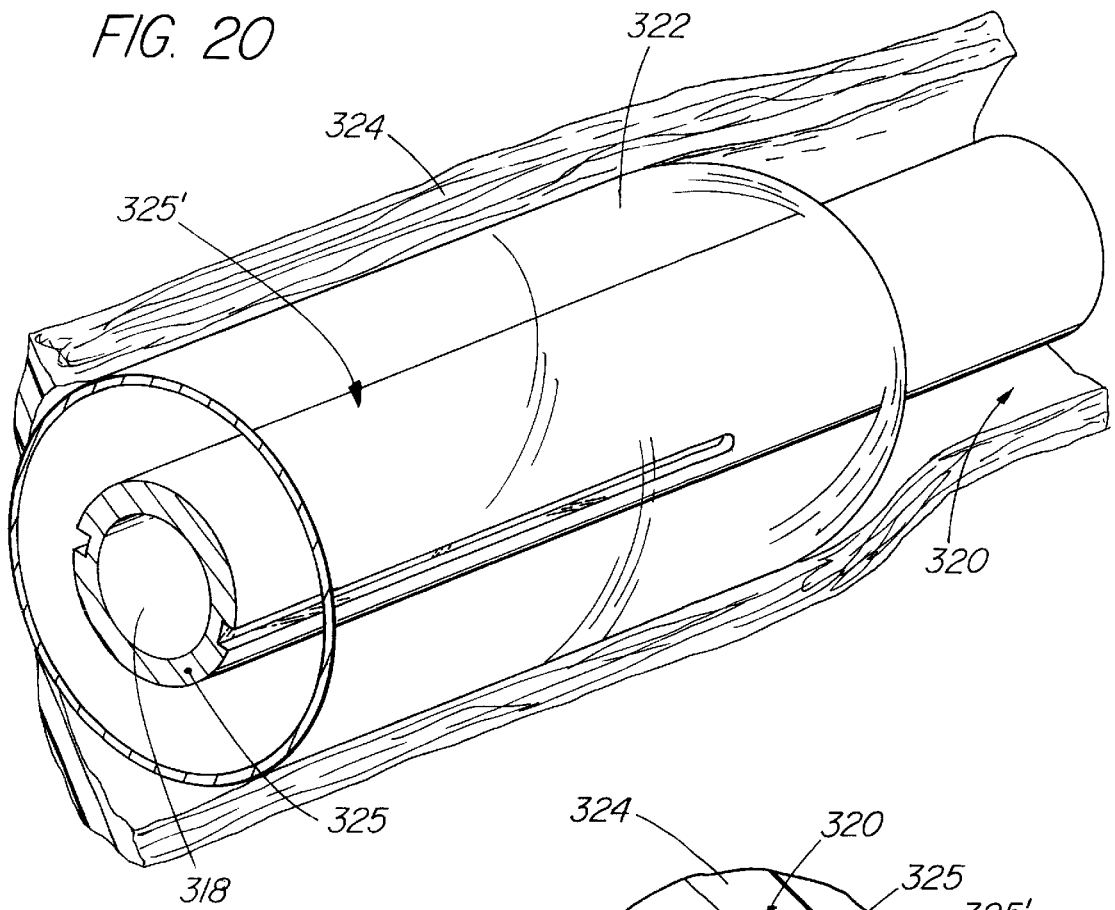
FIG. 20 is an enlarged partially sectional assembly drawing of a sixth embodiment of the catheter system of the present invention, with a single balloon fully inflated as the blood flows through the center section of the apparatus.
Figure 21:
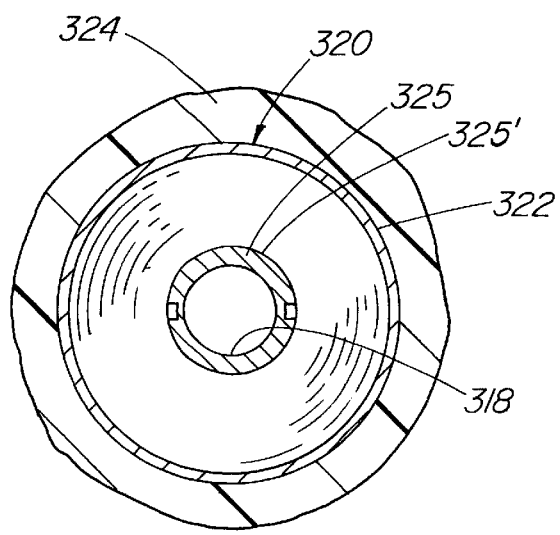
FIG. 21 is a cross-sectional end view of the catheter system of FIG. 20.

FIGS. 20 and 21 disclose yet another embodiment of the catheter apparatus 320, the catheter comprising an inner lumen 318 (with wall 325) for the transmission of blood when the catheter is inserted into a blood vessel. A specific coating of integrated and layered transitional metal or metal alloy compounds from the surface to the center of the exterior side 325' of the wall of the catheter lumen 318 protects the blood in the lumen from radiation, and enhances the radiation dosage delivered to the target. Either the heavy transitional metals or denser ranges of heavy metals are recommended, such as titanium, tungsten, aluminum, and germanium. The alloys can also include silicon. As used herein, the term "metal" includes pure metals, metal alloys, and metal alloy compounds.

FIG. 20 shows a balloon 322 extending around the inner lumen, and expanded by radiation fluid, the expanded balloon being in contact with the internal wall of a blood vessel 324. The lumen wall 325 attenuates the transmission dosage to the blood circulating through the hollow inner lumen of the central catheter apparatus 320. In addition, the system creates increased by-product radiation, bremsstrahlung and incidental scatter, from the impact of beta particles and gamma photons traveling into or toward the lumen wall 325. This energy, which would otherwise be wasted, produces by-product low-energy x-ray photons, which increase the deposited energy dosage into the target tissue via scattered angle coincidence or secondary redirected x-ray production from the slowing of beta particles traveling into or next to the metal compound on the wall surface 325'. These particles might ordinarily be considered too far from or having too little energy to reach the target tissue. However, the by-product x-rays (bremsstrahlung Radiation) travel through the balloon outer wall and deliver useful radiation dosage over a range of several hundred micrometers to the targeted tissue.

Figure 22:
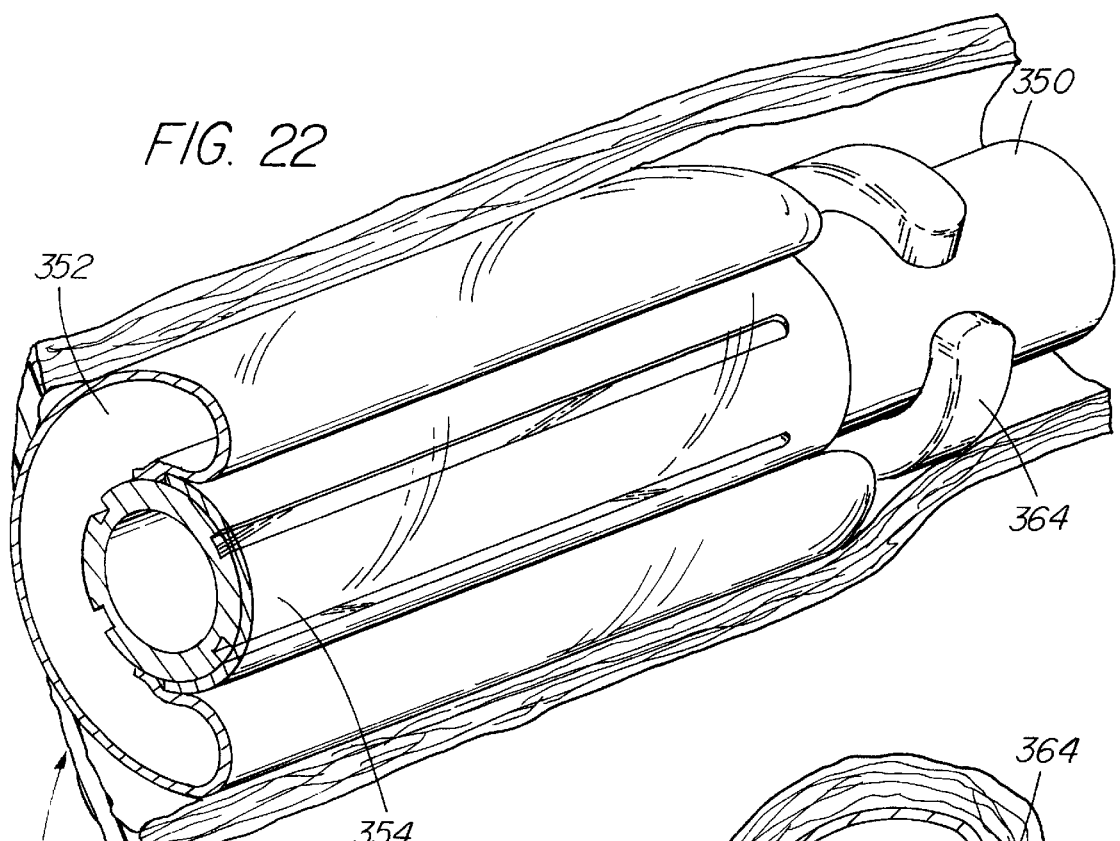
FIG. 22 is an enlarged partially sectional assembly drawing of a seventh embodiment of the catheter system of the present invention, with two separate, semi-circular balloons, one balloon being inflated and delivering a treatment dose, while the opposing balloon is deflated.
Figure 23:
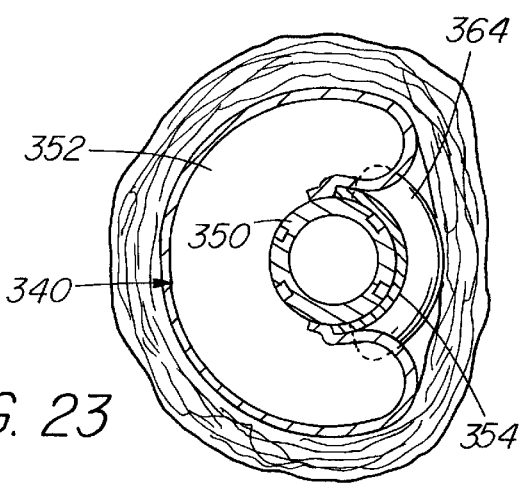
FIG. 23 is a cross-sectional end view of the catheter system of FIG. 22.
Figure 24:
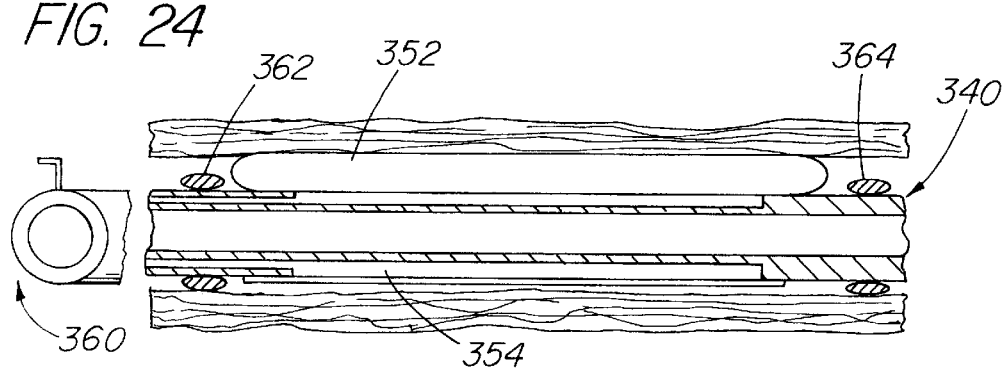
FIG. 24 is a longitudinal sectional side view of the catheter system of FIG. 22.

Still another catheter apparatus 340 is disclosed in FIGS. 22, 23 and 24. Two opposing and separate, semi-circular balloons 352 and 354 include opposed support displacers 362 and 364 attached just proximal and distal to the balloon lengths upon the outer lumen wall 350 of the inner lumen.

An injection port unit 360 enables fluid-tight redirection of radioactive fluid flow from between the balloons 352 and 354. Thereby, while one balloon 352 is inflated and delivering treatment dosage, the opposing balloon 354 is deflated. The support displacers 362 and 364 are juxtaposed against the vessel wall enabling blood to flow more easily through the space opposite to the treatment side.

The single-unit injection port 360 with synthetic septum is fluid-tight and leak-proof. The port 360 is preferably made of Viton rubber, enabling easy needle penetration without loss of gas under pressure via leaky adaptive Luerlock additions.

The radioactive xenon gas can be partially dissolved in sterile saline or lipid-containing solution for solubilizing the xenon. The resulting material can then be injected into a balloon system.

It is also contemplated that the dosimetry unit of measurement indicator 21 disposed, affixed, or positioned on a delivery device can be an electronic display panel such as LCD or LED. The display panel indicator can be connected to an electronic radiation sensor or detector positioned at that portion of the device for treating tissue. Such displays and detectors are commercially available.

What is claimed is:

1. A medical radiation treatment device containing a radioactive fluid to be delivered to a treatment site, comprising:
   a fluid-tight container having an interior volume in a range from more than 0 to 10 cubic centimeters; and
   a radioactive fluid in said fluid-tight container having a specific concentration in a range of 150 to 500 millicuries per cubic centimeter, whereby a preferred total activity in a range of 200 to 450 millicuries per administration suitable for effectively treating a patient is ready to be delivered to the treatment site.

2. The radiation treatment device of claim 1, wherein said radioactive fluid includes an inert radioactive gas.

3. The radiation treatment device of claim 1, wherein said radioactive fluid includes a carrier and a radioactive substance dispersed in said carrier.

4. The radiation treatment device of claim 3, wherein said carrier is at least 90% by volume of said radioactive fluid.

5. The radiation treatment device of claim 3, wherein said radioactive substance is at most 10% by volume of said radioactive fluid.

6. The radiation treatment device of claim 3, wherein said carrier is approximately 95% by volume of said radioactive fluid and wherein said radioactive substance is approximately no greater than 5% by total injected volume of said radioactive fluid.

7. The radiation treatment device of claim 3, wherein said radioactive substance includes an inert radioactive gas.

8. The radiation treatment device of claim 7, wherein said radioactive gas includes from a group consisting of xenon, krypton, neon, radon, and isotopes thereof.

9. The radiation treatment device of claim 7, wherein said radioactive gas includes xenon-127 or xenon-133.

10. The radiation treatment device of claim 3, wherein carrier includes sterile water, saline, carbon dioxide gas, or any non-radioactive inert or noble gas.

11. The radiation treatment device of claim 1, wherein said interior volume is in a range of 1 to 7 cubic centimeters.

12. The radiation treatment device of claim 1, wherein said interior volume is in a range of 2 to 6 cubic centimeters.

13. The radiation treatment device of claim 1, wherein said interior volume is in a range of 2 to 3 cubic centimeters.

14. The radiation treatment device of claim 1, wherein said fluid-tight (gas-tight) container includes a plunger base disposed in said interior volume for direct injection.

15. A sealed source of a radioactive fluid comprising:
    a fluid-tight container having an interior volume in a range of 2 to 6 cubic centimeters; and
    a radioactive fluid in said fluid-tight container having a specific concentration in a range of 150 to 225 millicuries per cubic centimeter, suitable for effectively treating a patient.

16. The sealed source of claim 15, wherein said radioactive fluid includes a carrier and a radioactive substance dispersed in said carrier.

17. The sealed source of claim 16, wherein said carrier comprises a carbon dioxide gas at least 90% by volume of said radioactive fluid and wherein said radioactive substance comprises a xenon gas having at most 10% by volume of said radioactive fluid.

18. The sealed source of claim 17, wherein said carbon dioxide gas is approximately 95% by volume of said radioactive fluid and wherein said xenon gas is xenon-133 and is approximately 5% by volume of said radioactive fluid.

19. A sealed source of radioactive gas comprising:
    a gas-tight container having an interior volume of approximately 3 cubic centimeters; and
    approximately 2 cubic centimeters of a radioactive gas including carbon dioxide gas of approximately 95% by volume of said radioactive gas and xenon-133 gas of approximately 5% by volume of said radioactive gas and having a specific concentration in a range of 150 to 225 millicuries per cubic centimeter, suitable for effectively treating a patient.

* * * * *